United States Patent
Lim et al.

(10) Patent No.: US 10,266,631 B2
(45) Date of Patent: Apr. 23, 2019

(54) METHOD FOR PREPARING PEPTIDE-POLYMER CONJUGATE WITH STABILIZED α-HELIX SECONDARY STRUCTURE AND PEPTIDE-POLYMER CONJUGATE PREPARED THEREBY

(71) Applicant: INDUSTRY-ACADEMIC COOPERATION FOUNDATION, YONSEI UNIVERSITY, Seoul (KR)

(72) Inventors: Yong-beom Lim, Seoul (KR); Young-joo Lee, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 161 days.

(21) Appl. No.: 15/419,446

(22) Filed: Jan. 30, 2017

(65) Prior Publication Data

US 2018/0051117 A1 Feb. 22, 2018

(30) Foreign Application Priority Data

Aug. 17, 2016 (KR) .................. 10-2016-0104089

(51) Int. Cl.
| | | |
|---|---|---|
| C08F 290/06 | (2006.01) | |
| C08F 289/00 | (2006.01) | |
| C07K 14/47 | (2006.01) | |
| C07K 7/08 | (2006.01) | |
| A61K 47/42 | (2017.01) | |
| A61K 47/58 | (2017.01) | |
| C08F 220/56 | (2006.01) | |

(52) U.S. Cl.
CPC .......... *C08F 290/065* (2013.01); *A61K 47/58* (2017.08); *C07K 14/4746* (2013.01)

(58) Field of Classification Search
CPC ................ C08F 289/00; C07K 7/08
USPC .......................... 525/54.1; 530/345
See application file for complete search history.

(56) References Cited

U.S. PATENT DOCUMENTS 6,565,842 B1 * 5/2003 Sojomihardjo ...... A61K 9/1652
424/178.1

FOREIGN PATENT DOCUMENTS

KR 1020160049529 5/2016

OTHER PUBLICATIONS

Han, et al, "Covalent Capture of alpha-Helical Peptides in Polymer Hydrogel Network for Polyacrylamide Gel Stabilization Electrophoresis," Journal of Polymer Science, Part A: Polymer Chemistry 2014, 52, 596-599. (Year: 2014).*
Lee, et al, "Simultaneous Stabilization and Multimerization of a Peptide alpha-Helix by Stapling Polymerization," Macromol. Rapid Communication, 2016, 37, 1021-1026 (Published Online: May 10, 2016). (Year: 2016).*
Sadler, et al., "Synthetic peptide epitope-based polymers: controlling size and determining the efficiency of epitope incorporation", J. Peptide Res., 2002, 60, pp. 150-158.

* cited by examiner

*Primary Examiner* — Fred M Teskin
(74) *Attorney, Agent, or Firm* — Duane Morris LLP; Gregory M. Lefkowitz; Jason M. Nolan

(57) ABSTRACT

A peptide-polymer conjugate prepared by a method for preparing a peptide-polymer conjugate according to the present disclosure stably maintains the two-dimensional structure of multiple α-helix ligands so that its biological interaction is improved while maintaining the specific structure of the peptide ligands.

17 Claims, 20 Drawing Sheets

Specification includes a Sequence Listing.

bisAAm-p53  Ac-QSQQTF-K(ε-acryloyl)-NLWRLL-K(ε-acryloyl)-QN-NH$_2$
                        *i*                    *i+7*

FAM-bisAAM-p53  FAM-QSQQTF-K(ε-acryloyl)-NLWRLL-K(ε-acryloyl)-QN-NH$_2$
                          *i*                    *i+7* bisAAm-BH3

METHOD FOR PREPARING PEPTIDE-POLYMER CONJUGATE WITH STABILIZED α-HELIX SECONDARY STRUCTURE AND PEPTIDE-POLYMER CONJUGATE PREPARED THEREBY

CROSS-REFERENCE TO RELATED APPLICATIONS

This application claims, under 35 U.S.C. § 119, the priority of Korean Patent Application No. 10-2016-0104089 filed on Aug. 17, 2016 in the Korean Intellectual Property Office, the disclosure of which is incorporated herein by reference in its entirety.

TECHNICAL FIELD

The present disclosure relates to a method for synthesis of a peptide-polymer conjugate, more particularly to a method for preparing a new peptide-polymer conjugate using stapling polymerization for stabilization and multimerization of an α-helix peptide and a peptide-polymer conjugate prepared thereby.

BACKGROUND

In general, biomacromolecules have superior affinity and selectivity for specific target materials in order to perform biological functions.

The most important factor in the activity of the biomacromolecules is the folded structure of peptides constituting the biomacromolecules. The folded structure, or the secondary structure, of the peptides can be stably controlled by maintaining specific environmental conditions. However, when the peptides are separated from the biomacromolecules (e.g., proteins), the peptides are unfolded as inactive random coils as the folded structure of the peptides is destabilized.

To solve this problem, there have been various studies aimed to stabilize the secondary structure of peptides for a long time without influence from surroundings. Most of these studies are about peptides with α-helix secondary structures which are the most frequently used among the biomacromolecules and have the most important activities.

As the most representative example of these studies, an invention of self-assembling peptides into cyclic molecules such that the α-helix secondary structures of the peptides are stabilized in the cycles has been presented.

The preparation of the cyclic peptides is limited in terms of commercialization due to the problems of a complicated process, low yield and difficult purification as compared to the synthesis of linear peptides. Furthermore, there is a fundamental limitation in that the peptide monomer has specificity for only one interaction and cannot target multiple interactions.

The inventors of present disclosure have made efforts to overcome the problems described above and provide a one-pot synthesis method for constructing a peptide with multiple α-helix secondary structures and have completed the present disclosure.

REFERENCES OF THE RELATED ART

Patent Documents

Korean Patent Publication No. 10-2016-0049529.

SUMMARY

The present disclosure is directed to providing a method for preparing a peptide-polymer conjugate.

The present disclosure is also directed to providing an α-helix peptide substituted with an acryloyl group.

The present disclosure is also directed to providing a peptide-polymer conjugate formed from polymerization of the α-helix peptide substituted with an acryloyl group.

In an aspect, the present disclosure provides a method for preparing a peptide-polymer conjugate, which includes:

I) a step of synthesizing an α-helix peptide substituted with an acryloyl group; and II) a step of polymerizing the acryloyl group of the α-helix peptide substituted with an acryloyl group synthesized in the step I) into polyacrylamide by dissolving the α-helix peptide substituted with an acryloyl group synthesized in the step I), a water-soluble monomer and a polymerization initiator in a solvent.

The α-helix peptide substituted with an acryloyl group in the step I) may be an α-helix peptide having at least two lysine residues, and two lysine residues in the α-helix peptide may have the hydrogen of the side-chain amine group (ε-amine group) substituted with an acryloyl group.

The two lysine residues may be formed necessarily at accurate positions in the α-helix peptide, with one lysine residue located at i-th position and the other lysine residue located at (i+7)-th position.

The α-helix peptide substituted with an acryloyl group in the step I) may have the at least two lysine residues, two lysine residues are necessarily located at i-th position and (i+7)-th position in the α-helix peptide, and the hydrogen of the side-chain amine group (ε-amine group) of the lysine residues located at i-th position and (i+7)-th position may be substituted with an acryloyl group.

The α-helix peptide having the at least two lysine residues may be an α-helix peptide selected from a group consisting of SEQ ID NOS 1 to 10.

The solvent may be one or more selected from a group consisting of a Tris buffer, a phosphate buffer, phosphoric acid, acetic acid, formic acid, hydrochloric acid, sulfuric acid, nitric acid, citric acid, hexafluoroisopropanol (HFIP), hexafluoropropanol (HFP), hexafluoroacetone (HFA), trifluoroacetic acid (TFA), diisopropylethylamine and methylimidazolium chloride.

The water-soluble monomer may be one or more selected from a group consisting of acrylamide, acrylonitrile, acryloyl chloride, methacrylamide, N-hydroxymethylacrylamide, N,N-dimethylacrylamide, N-acetamidoacrylamide, 2-aminoethyl methacrylate, N,N-dimethylaminoethyl methacrylate, allyl alcohol, 2-hydroxyethyl acrylate, 2-hydroxyethyl methacrylate and 2-hydroxypropyl methacrylate.

The polymerization initiator may be one or more selected from a group consisting of azobisisobutyronitrile (AIBN), ammonium persulfate (APS) and N,N,N',N'-tetramethylenediamine (TEMED).

The α-helix peptide substituted with an acryloyl group synthesized in the step I) and the water-soluble monomer may be mixed at a molar ratio of 1:10 to 1:100.

In another aspect, the present disclosure provides an α-helix peptide substituted with an acryloyl group, wherein the α-helix peptide has at least two lysine residues, with one lysine residue located at i-th position and another lysine residue located at (i+7)-th position in the α-helix peptide, and the hydrogen of the side-chain amine group of the two lysine residues located at i-th position and (i+7)-th position is substituted with an acryloyl group.

The α-helix peptide may be one or more selected from SEQ ID NOS 1 to 10.

In another aspect, the present disclosure provides a peptide-polymer conjugate having a polymerized linear polymer formed from polymerization of the acryloyl group of the α-helix peptide substituted with an acryloyl group and a water-soluble monomer as a main chain, wherein at least one α-helix peptide is fixed to the polymerized linear polymer.

The α-helix peptide may be one or more selected from SEQ ID NOS 1 to 10.

In the peptide-polymer conjugate, the α-helix secondary structure of the α-helix peptide may be stabilized.

The peptide-polymer conjugate may have a $[\theta]_{208}/[\theta]_{222}$ ratio of 1-1.5 in a CD spectrum at 0-60° C.

The peptide-polymer conjugate may maintain a $[\theta]_{208}/[\theta]_{222}$ ratio of 0.8 or greater in a CD spectrum at 0-100° C.

3-20 α-helix peptides may be fixed in the peptide-polymer conjugate.

The method for preparing a peptide-polymer conjugate according to the present disclosure, wherein the specific secondary structure of the peptide is maintained stably and a plurality of peptides are fixed on the linear polymer, is advantageous in that the peptide-polymer conjugate can be synthesized conveniently and easily through a single process.

According to the method for preparing a peptide-polymer conjugate, a plurality of peptides can be simultaneously fixed on the linear polymer and biological interaction can be effectively improved by stabilizing the secondary structure.

The novel peptide-polymer conjugate and the new method for preparing the same are based on radical polymerization between the peptide substituted with an acryloyl group and the water-soluble monomer. This is the simplest and the most powerful synthesis method for preparing α-helix peptide-polymer conjugates developed for controlling interaction between multivalent biomacromolecules.

In addition, the peptide-polymer conjugate prepared according to the above-described preparation method is applicable to various applications because a plurality of peptides having identical or different activities can be fixed simultaneously.

BRIEF DESCRIPTION OF DRAWINGS

In FIG. 15, M represents a protein marker and P represents a peptide-polymer conjugate prepared in Example 5. The image on the right side is a fluorescence image.

DETAILED DESCRIPTION OF EMBODIMENTS

Hereinafter, various aspects and exemplary embodiments of the present disclosure are described in detail.

Figure 1A:
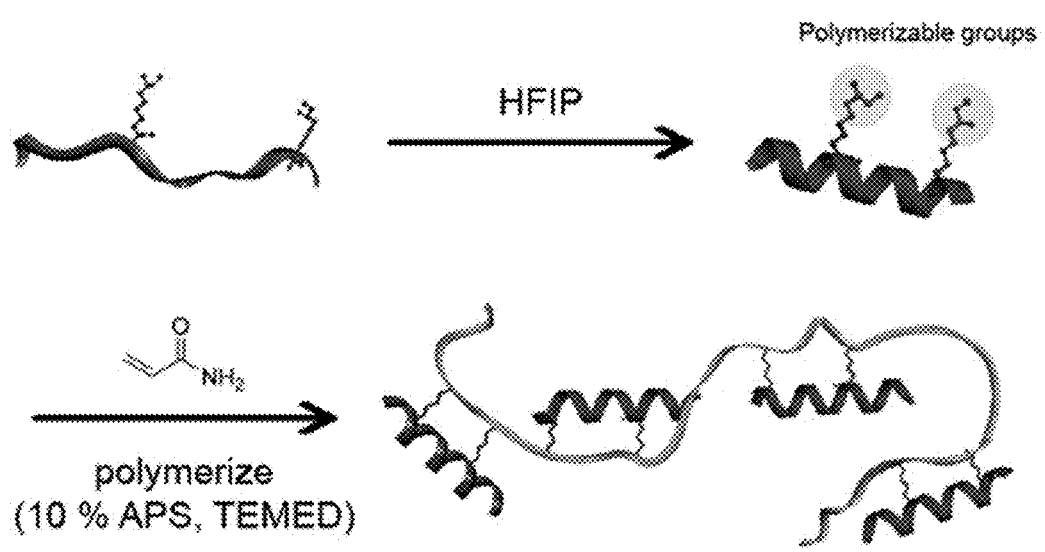
FIG. 1A schematically describes a synthesis process of a peptide-polymer conjugate according to the present disclosure.

In an aspect, the present disclosure relates to a method for preparing a peptide-polymer conjugate, which includes: I) a step of synthesizing an α-helix peptide substituted with an acryloyl group; and II) a step of polymerizing the acryloyl group of the α-helix peptide substituted with an acryloyl group synthesized in the step I) into polyacrylamide by dissolving the α-helix peptide substituted with an acryloyl group synthesized in the step I), a water-soluble monomer and a polymerization initiator in a solvent. The method is described in detail in FIG. 1A.

Figure 1B:
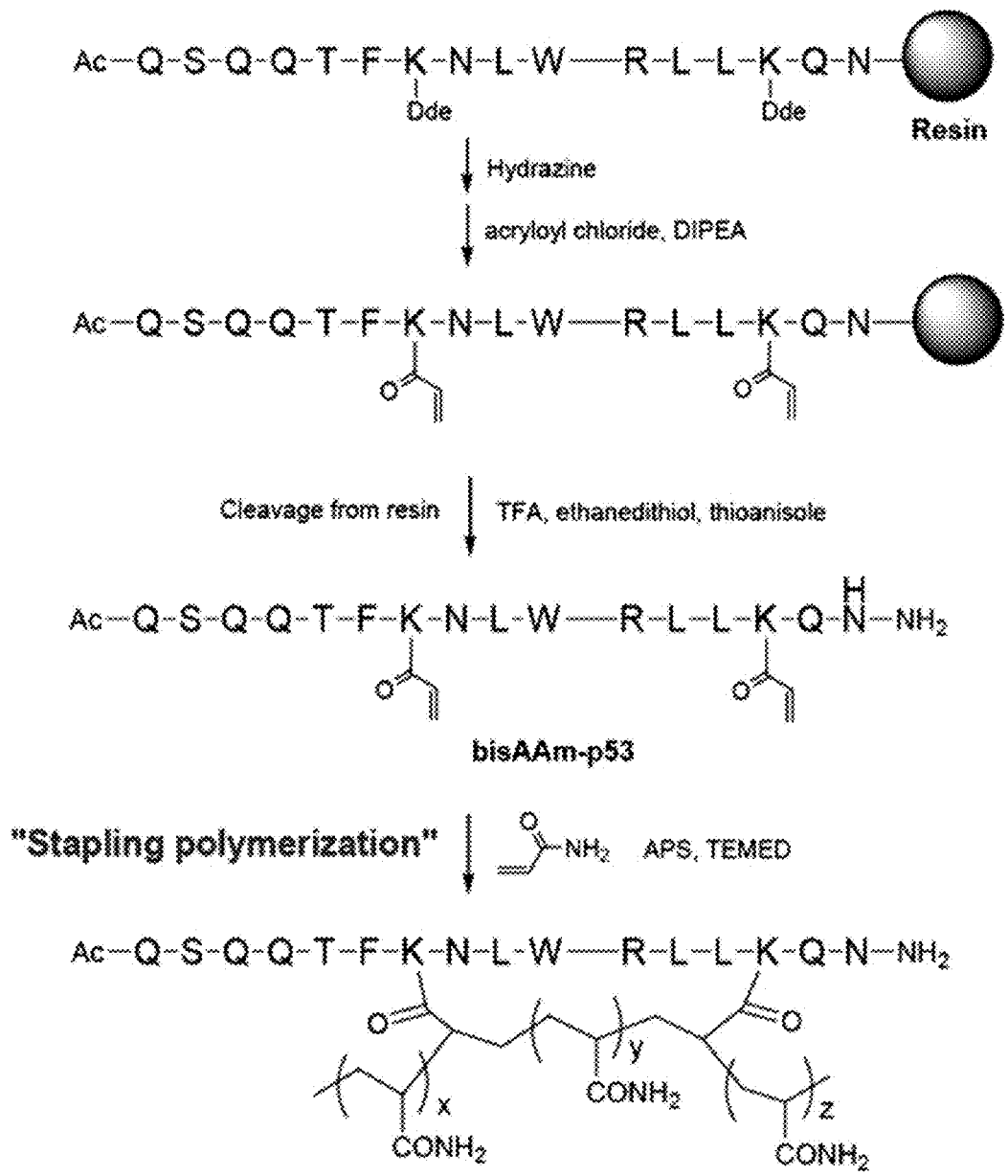
FIG. 1B specifically describes an overall synthesis process of a peptide-polymer conjugate in Example 1 according to the present disclosure.

The α-helix peptide substituted with an acryloyl group of the step I) may be synthesized by a common preparation method without limitation. Specifically, it may be synthesized by using the Fmoc solid-phase peptide synthesis protocol. Specifically, it may be synthesized through the following procedure using the Fmoc solid-phase peptide synthesis protocol:

i) a step of binding a first amino acid residue to a solid-phase resin;

ii) a step of removing an Fmoc protecting group from the first amino acid residue and connecting a second amino acid residue to the first amino acid residue;

iii) a step of synthesizing an α-helix peptide selected from SEQ ID NOS 1 to 10 wherein only the side-chain amine group (ε-amine group) of two lysine residues located at i-th and (i+7)-th positions is protected with a Dde protecting group;

iv) a step of removing the Dde protecting group protecting the side-chain amine group (ε-amine group) of the two lysine residues located at i-th and (i+7)-th positions in the α-helix peptide and synthesizing an α-helix peptide substituted with an acryloyl group by substituting the hydrogen of the side-chain amine group (ε-amine group) of the lysine residues with an acryloyl group; and v) a step of separating the α-helix peptide substituted with an acryloyl group from the solid-phase resin (FIG. 1B).

The α-helix peptide in the step iii) may be an α-helix peptide having at least two lysine residues, and one of the two lysine residues may be located at i-th position in the α-helix peptide and the other lysine residue may be located at (i+7)-th position. More specifically, it may be one selected from SEQ ID NOS 1 to 10.

That is to say, through the synthesis of the peptide (by repeating the step ii)), an α-helix peptide selected from a group consisting of SEQ ID NOS 1 to 10 having at least two lysine residues is synthesized. Specifically, the lysine residues located at i-th and (i+7)-th positions may be necessarily synthesized using an amino acid residue with a side-chain amine group (ε-amine group) protected with a Dde protecting group and the remaining amino acid residues (including lysine residues not located at i-th and (i+7)-th positions) may be protected with a protecting group other than the Dde protecting group.

Through this, an α-helix peptide selected from SEQ ID NOS 1 to 10 wherein only the side-chain amine group (ε-amine group) of the two lysine residues located at i-th and (i+7)-th positions is protected with a Dde protecting group is synthesized.

In an exemplary embodiment of the present disclosure, when the α-helix peptide having the structure described above is used, although the peptide has two or more lysine residues, only the side-chain amine group (ε-amine group) of the lysine residues located at i-th and (i+7)-th positions may be substituted with an acryloyl group in the following step because only the side-chain amine group (ε-amine group) of the lysine residues located at i-th and (i+7)-th positions is protected with the Dde protecting group.

Most specifically, an α-helix peptide having lysine residues located only at i-th and (i+7)-th positions, as SEQ ID NO 1, may be used to prepare an α-helix peptide with only the hydrogen at the side-chain amine group (ε-amine group) of the lysine residues located at i-th and (i+7)-th positions substituted with an acryloyl group.

For the step iv), the α-helix peptide may be mixed in a 2-5% hydrazine solution in DMF and then the mixture may be treated with 10 equivalents of acryloyl chloride and 20 equivalents of a DIPEA solution in NMP.

Through this process, an α-helix peptide substituted with an acryloyl group wherein only the hydrogen of the side-chain amine group of the two lysine residues located at i-th and (i+7)-th positions of the α-helix peptide is substituted with the acryloyl group may be synthesized.

The α-helix peptide substituted with an acryloyl group is synthesized through the above-described process. The α-helix peptide substituted with an acryloyl group of the step I) may have the at least two lysine residues, and the two lysine residues of the α-helix peptide may necessarily have the hydrogen of the side-chain amine group (ε-amine group) substituted with the acryloyl group.

In the α-helix peptide, the two lysine residues may be necessarily located at accurate positions, with one lysine residue located at i-th position and the other lysine residue located at (i+7)-th position.

The α-helix peptide substituted with an acryloyl group of the step I) may have the at least two lysine residues and the two lysine residues of the α-helix peptide may be necessarily located at i-th and (i+7)-th positions. And, the hydrogen of the side-chain amine group (ε-amine group) of the lysine residues located at i-th and (i+7)-th positions may be substituted with an acryloyl group.

The α-helix peptide having the at least two lysine residues may be an α-helix peptide selected from a group consisting of SEQ ID NOS 1 to 10.

p53 peptide
[SEQ ID NO 1]
Gln Ser Gln Gln Thr Phe Lys Asn Leu Trp Arg Leu
Leu Lys Gln Asn p53 peptide
[SEQ ID NO 2]
Gln Ser Gln Gln Thr Phe Lys Asn Leu Trp Lys Leu
Leu Lys Gln Asn p53 peptide
[SEQ ID NO 3]
Leu Ser Gln Gln Thr Phe Lys Asn Leu Trp Arg Leu
Leu Lys Gln Asn p53 peptide
[SEQ ID NO 4]
Leu Ser Gln Glu Thr Phe Lys Asn Leu Trp Lys Leu
Leu Lys Gln Asn p53 peptide
[SEQ ID NO 5]
Leu Ser Gln Glu Thr Phe Lys Asp Leu Trp Lys Leu
Leu Lys Glu Asn p53 peptide
[SEQ ID NO 6]
Leu Ser Gln Lys Thr Phe Ser Asp Leu Trp Lys Leu
Leu Pro Glu Asn p53 peptide
[SEQ ID NO 7]
Leu Ser Gln Glu Lys Phe Ser Asp Leu Trp Lys Lys
Leu Pro Glu Asn p53 peptide
[SEQ ID NO 8]
Leu Ser Gln Glu Thr Phe Ser Asp Lys Trp Lys Leu
Leu Pro Glu Lys p53 wild type peptide
[SEQ ID NO 9]
Leu Ser Gln Glu Thr Phe Lys Asp Lys Trp Arg Leu
Leu Lys Gln Asn p53 wild type peptide
[SEQ ID NO 10]
Gln Ser Gln Gln Thr Phe Lys Asn Leu Trp Arg Lys
Lys Lys Gln Asn In the step II), the acryloyl group of the α-helix peptide substituted with an acryloyl group synthesized in the step I)

and a water-soluble monomer are polymerized by dissolving the α-helix peptide substituted with an acryloyl group synthesized in the step I), the water-soluble monomer and a polymerization initiator in a solvent.

The solvent may be one or more selected from a group consisting of a Tris buffer, a phosphate buffer, phosphoric acid, acetic acid, formic acid, hydrochloric acid, sulfuric acid, nitric acid, citric acid, hexafluoroisopropanol (HFIP), hexafluoropropanol (HFP), hexafluoroacetone (HFA), trifluoroacetic acid (TFA), diisopropylethylamine, and methylimidazolium chloride. Specifically, HFIP which maintains the α-helix secondary structure of the α-helix peptide most stably may be used.

The water-soluble monomer may be one or more selected from a group consisting of acrylamide, acrylonitrile, acryloyl chloride, methacrylamide, N-hydroxymethylacrylamide, N,N-dimethylacrylamide, N-acetamidoacrylamide, 2-aminoethyl methacrylate, N,N-dimethylaminoethyl methacrylate, allyl alcohol, 2-hydroxyethyl acrylate, 2-hydroxyethyl methacrylate and 2-hydroxypropyl methacrylate. Specifically, acrylamide may be used as the water-soluble monomer.

The polymerization initiator may be one or more selected from a group consisting of azobisisobutyronitrile (AIBN), ammonium persulfate (APS) and N, N,N',N'-tetramethylenediamine (TEMED).

When the α-helix peptide substituted with an acryloyl group synthesized in the step I) and the water-soluble monomer are mixed at a molar ratio of 1:10 to 1:100, a peptide-polymer conjugate with a stably formed α-helix secondary structure may be obtained. Specifically, in order to prepare a peptide-polymer conjugate with a very stable α-helix secondary structure, with a negative peak intensity ratio at 208 nm and 222 nm ($[\theta]_{222}/[\theta]_{208}$ ratio) in a CD spectrum of 1 or greater (0-60° C.), they may be mixed at a molar ratio of 1:15 to 1:25.

In another aspect, the present disclosure relates to an α-helix peptide substituted with an acryloyl group, wherein the α-helix peptide has at least two lysine residues, with one lysine residue located at i-th position and another lysine residue located at (i+7)-th position in the α-helix peptide, and the hydrogen of the side-chain amine group of the two lysine residues located at i-th position and (i+7)-th position is substituted with an acryloyl group. An exemplary structure is shown FIG. 2B.

If, in the α-helix peptide, one lysine residue is located at i-th position and the other lysine residue is located at (i+4)-th position, the α-helix secondary structure may not be sufficiently fixed in the peptide-polymer conjugate to be formed but unfolded, thereby failing to maintain the activity of the peptide. Therefore, specifically, the α-helix peptide may have one lysine residue located at i-th position and the other lysine residue located at (i+7)-th position.

That is to say, because the α-helix peptide has 3.6 residues per turn of the α-helix secondary structure and because i-th and (i+7)-th residues among them are arranged in the same direction, the peptide having the α-helix secondary structure wherein lysine residues are located at the above-described positions or the existing peptide having an α-helix secondary structure wherein the residues are located at the above-described positions are substituted with lysine residues may be used.

According to the present disclosure, a peptide-polymer conjugate may be prepared using any peptide which has an α-helix secondary structure and has lysine residues located at i-th and (i+7)-th positions.

This can be inferred from that, as demonstrated in the test examples to be described below, α-helix peptides substituted with an acryloyl group are prepared from SEQ ID NOS 1 to 10 (e.g., peptides derived from p53) having lysine residues at i-th and (i+7)-th positions and peptide-polymer conjugates wherein the α-helix secondary structure is stably constrained are prepared therefrom.

In other words, when preparing the α-helix peptide substituted with an acryloyl group of the present disclosure, the amino acid sequence of the α-helix peptide is not particularly limited as long as one lysine residue is located at i-th position and the other lysine residue is located at (i+7)-th position in the α-helix peptide.

More specifically, the α-helix peptide may be one or more of SEQ ID NOS 1 to 10. More specifically, the α-helix peptide may be SEQ ID NO 1 or 2.

If the α-helix peptide is not one in which one lysine residue is located at i-th position and the other lysine residue is located at (i+7)-th position in the α-helix peptide, the α-helix secondary structure is destabilized and unfolded in a peptide-polymer conjugate to be formed.

The α-helix peptide substituted with an acryloyl group may further contain a fluorophore at the C-terminal. The fluorophore may be selected from a group consisting of DEABA, Dapoxyl and carboxyfluorescein (FAM), although not being particularly limited thereto.

Figure 16A:
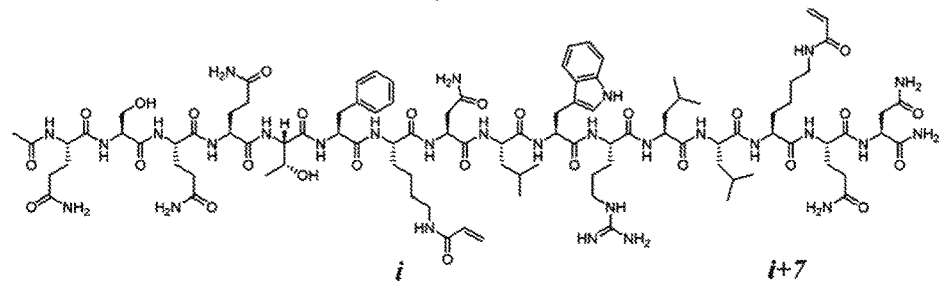
FIG. 16A shows the structure of an α-helix peptide substituted with an acryloyl group of Preparation Example 1, according to the present disclosure.
Figure 16B:
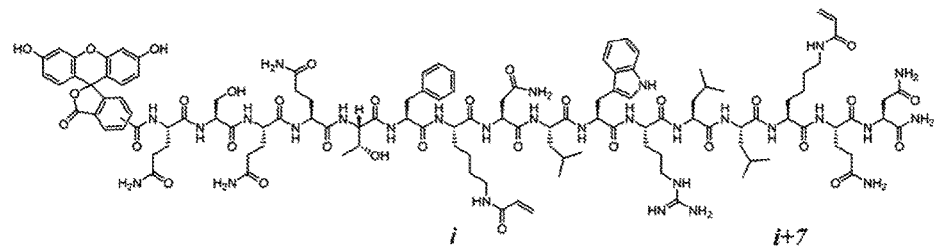
FIG. 16B shows the structure of an α-helix peptide substituted with an acryloyl group of Preparation Example 2, according to the present disclosure.

Specifically, the α-helix peptide substituted with an acryloyl group according to the present disclosure may be one having a structure selected from the compound shown in FIG. 16A and the compound shown in FIG. 16B.

The α-helix peptide substituted with an acryloyl group according to the present disclosure of the above structure exhibits biological activity only in the presence of an α-helix stabilizer (HFIP) where the α-helix secondary structure is stably maintained. In contrast, a peptide-polymer conjugate prepared based thereon exhibits a negative peak intensity ratio at 208 nm and 222 nm ($[\theta]_{222}/[\theta]_{208}$ ratio) in a CD spectrum of 1 or greater (0-60° C.) not only in the presence of an α-helix stabilizer but also in a general buffer or distilled water absolutely free of an α-helix stabilizer.

That is to say, the peptide-polymer conjugate according to the present disclosure has a very stable α-helix secondary structure regardless of the solvent.

In another aspect, the present disclosure relates to a having a polymerized linear polymer formed from polymerization of the acryloyl group of the α-helix peptide substituted with an acryloyl group and a water-soluble monomer as a main chain, wherein at least one α-helix peptide is fixed to the polymerized linear polymer.

In general, for a particular biomacromolecule to specifically bind to a particular target substance and to effectively exert interaction, it needs to have superior affinity and selectivity for the target substance.

The affinity and selectivity of the biomacromolecule are greatly dependent on whether the structural stability of the secondary structure of a peptide functioning as a ligand is maintained.

Conventionally, in order to constrain and stabilize the secondary structure of the peptide by reducing conformational entropy, a cyclic peptide was synthesized by cyclizing one α-helix peptide.

However, the cyclic peptide has problems of a difficult synthesis process, low yield and complicated purification process. In addition, because only one cyclic peptide can be prepared from one peptide monomer, it is impossible to target multiple interactions.

In contrast, the present disclosure provides a peptide-polymer conjugate wherein a plurality of α-helix peptides are bound and the stable α-helix secondary structure is effectively maintained, which can be synthesized very conveniently and easily through simple mixing.

The peptide-polymer conjugate according to the present disclosure is formed from polymerization of the acryloyl group of the α-helix peptide substituted with an acryloyl group and the water-soluble monomer. A linear polymer polymerized from the acryloyl group and the water-soluble monomer are polymerized serves as a main chain and at least one α-helix peptide is fixed to the linear polymer. This structure is specifically described in FIG. 2A.

Figure 2A:
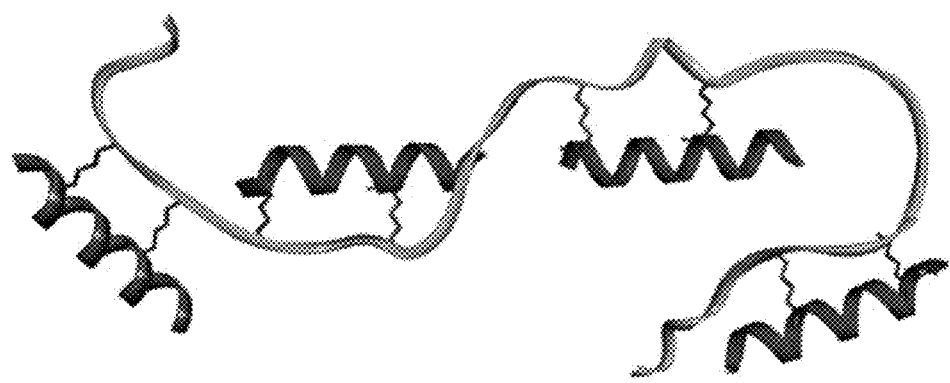
FIG. 2A shows the structure of a peptide-polymer conjugate according to the present disclosure.
Figure 2B:
FIG. 2B shows the structure of an α-helix peptide substituted with an acryloyl group according to the present disclosure.

In FIG. 2A, the red portions indicate the α-helix peptide, the blue portions indicate the linear polymer and the black lines indicate parts (hydrocarbon moieties) of the side-chain amine groups of lysines of the α-helix peptide as bridges connecting the α-helix peptide and the linear polymer.

Because the linear polymer is formed from polymerization of the acryloyl group which has substituted the hydrogen of the side-chain amine group of the lysine of the α-helix peptide and the water-soluble monomer, the hydrocarbon moiety of the side-chain amine group of the lysine serves as a bridge connecting the α-helix peptide and the linear polymer.

The α-helix peptide fixed on the polymerized linear polymer forms a macrocyclic bridge with the linear polymer by the side-chain amine group of the lysine residue bound to the acryloyl group and, thereby, constrains and stabilizes the α-helix secondary structure.

The α-helix peptide substituted with an acryloyl group may be an α-helix peptide substituted with an acryloyl group with the same or difficult amino acid sequences.

Accordingly, the peptide-polymer conjugate may be controlled to have single or multiple activities depending on the α-helix peptide.

Because the peptide-polymer conjugate has a plurality of identical or different α-helix peptides fixed on the linear polymer, the α-helix secondary structure present in the α-helix peptide can be constrained stably without being unfolded.

More specifically, the peptide-polymer conjugate has a $[\theta]_{208}/[\theta]_{222}$ ratio of 1-1.5 in a CD spectrum at 0-60° C., which indicates that the secondary structure of the peptide-polymer conjugate according to the present disclosure is maintained very stably.

In particular, the peptide-polymer conjugate maintains a $[\theta]_{208}/[\theta]_{222}$ ratio of 0.8 or greater in a CD spectrum at 0-100° C., suggesting that the secondary structure is maintained very stably even at high temperature.

The peptide-polymer conjugate may have 3-20 α-helix peptides fixed on the linear polymer.

The peptide-polymer conjugate according to the present disclosure stably maintains the secondary structure of the peptide in the peptide-polymer conjugate not only under an in-vivo condition (Tris buffer or phosphate buffer) but also at high temperature of 100° C., with a $[\theta]_{208}/[\theta]_{222}$ ratio of 0.8 or greater.

Through this, it is expected that the peptide-polymer conjugate according to the present disclosure can be applied to various drug delivery systems, sensors, diagnoses, etc. because it contains α-helix peptides having various biological activities and can stably maintain the secondary structure for a long time even at high temperature.

Hereinafter, the present disclosure will be described in more detail through specific examples so that those of ordinary skill in the art to which the present disclosure can easily carry out the present disclosure. However, the present disclosure can be embodied in various forms and is not limited to the examples.

Reagents

Fmoc-amino acids and coupling reagents were purchased from AnaSpec (USA). General chemicals were purchased from Novabiochem (Germany). All other reagents were purchased from Sigma-Aldrich (USA).

Measurement Methods

1) Circular Dichroism Spectroscopy

CD spectra were recorded using a Chirascan circular dichroism spectrometer equipped with a Peltier temperature controller (Applied Photophysics Ltd.). The CD spectra of peptides were recorded at 190-260 nm.

2) SDS-PAGE

A peptide-polymer conjugate of Example 2 prepared using an α-helix peptide substituted with an acryloyl group labeled with a fluorophore (Preparation Example 2; FAM-bisAAm-p53) was mixed in a 2× tricine sample buffer, freeze-dried and then heated at 90° C. for 10 minutes. SDS-PAGE was conducted using a Tris-tricine polyacrylamide gel containing 10% acrylamide gel. For the electrophoresis, an upper buffer containing 0.1 M Tris, 0.1 M tricine and 0.1% SDS and a 0.2 M Tris lower buffer adjusted to pH 8.9 were used as electrophoresis buffers. The electrophoresis was conducted at 120 V and the result was observed by irradiating UV to the gel after the electrophoresis was completed.

Preparation Examples 1-3. Synthesis of Peptides Substituted with Acryloyl Group

In order to synthesize peptides substituted with an acryloyl group, peptides having amino acid sequences described in Table 1 were prepared and the hydrogen of the side-chain amine group (ε-amine group) of the lysine residue present in the synthesized peptides was substituted with an acryloyl group (Table 2).

TABLE 1

| Peptide (SEQ ID NO) | Sequence |
| --- | --- |
| p53 (SEQ ID NO 1) | Ac-QSQQTFKNLWRLLKQN-NH$_2$ |
| BH3 (SEQ ID NO 2) | Ac-EDIIRNIARHLAKVGDKNLDRSIW-NH$_2$ |

TABLE 2

Figure 16C:
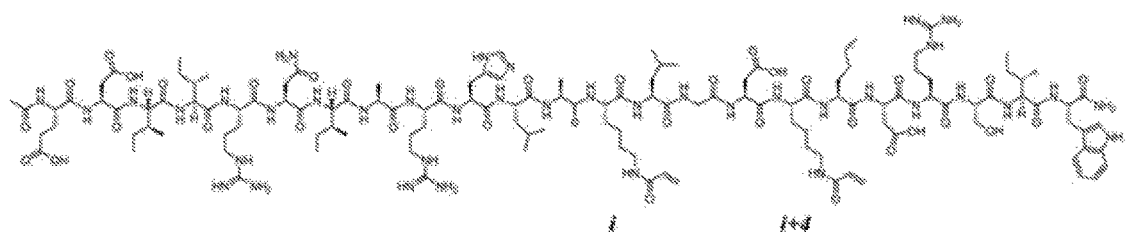
FIG. 16C shows the structure of an α-helix peptide substituted with an acryloyl group of Preparation Example 3, according to the present disclosure.

| Peptide | Sequence |
| --- | --- |
| bisAAm-p53 (Preparation Example 1) | see FIG. 16A |
| FAM-bisAAm-p53 (Preparation Example 2) | see FIG. 16B |
| bisAAm-BH3 (Preparation Example 3) | see FIG. 16C |

The peptide of SEQ ID NO 1 was synthesized using the Rink Amide MBHA resin LL (Novabiochem) according to the standard Fmoc protocol of the Tribute™ peptide synthesizer (Protein Technologies Inc.) and 2-(1H-benzotriazole-1-yl)-1,1,3,3-tetramethyluronium hexafluorophosphate (HBTU) was used as a coupling agent.

Standard amino acid protecting groups were used for residues except Lys. The ε-amine group of the lysine (Lys)

residue was protected using N-[1-(4,4-dimethyl-2,6-dioxo-cyclohex-1-ylidene)ethyl] (Dde) as a protecting group.

For acetylation, the resin (50 μmol of N-terminal amine groups) was mixed with equivalents (eq) of acetic anhydride and 20 equivalents (eq) of diisopropylethylamine (DIPEA) (in N-methyl-2-pyrrolidone (NMP)) for 3 hours. Then, the resin was washed with NMP and dimethylformamide (DMF) and the Dde protecting group protecting the side-chain amine group of the lysine residue was removed using a 2% hydrazine solution in DMF.

For acryloylation, the resin was treated with 10 equivalents of acryloyl chloride and 20 equivalents of a DIPEA solution in NMP for 3 hours.

Fluorophore-labeled peptides were prepared by binding 5(6)-carboxyfluorescein to the N-terminal of the peptide bound to the resin according to the standard Fmoc protocol and conducting coupling reactions overnight using 2-(7-aza-1H-benzotriazole-1-yl)-1,1,3,3-tetramethyluronium hexafluorophosphate (HATU) instead of HBTU.

Figure 17A:
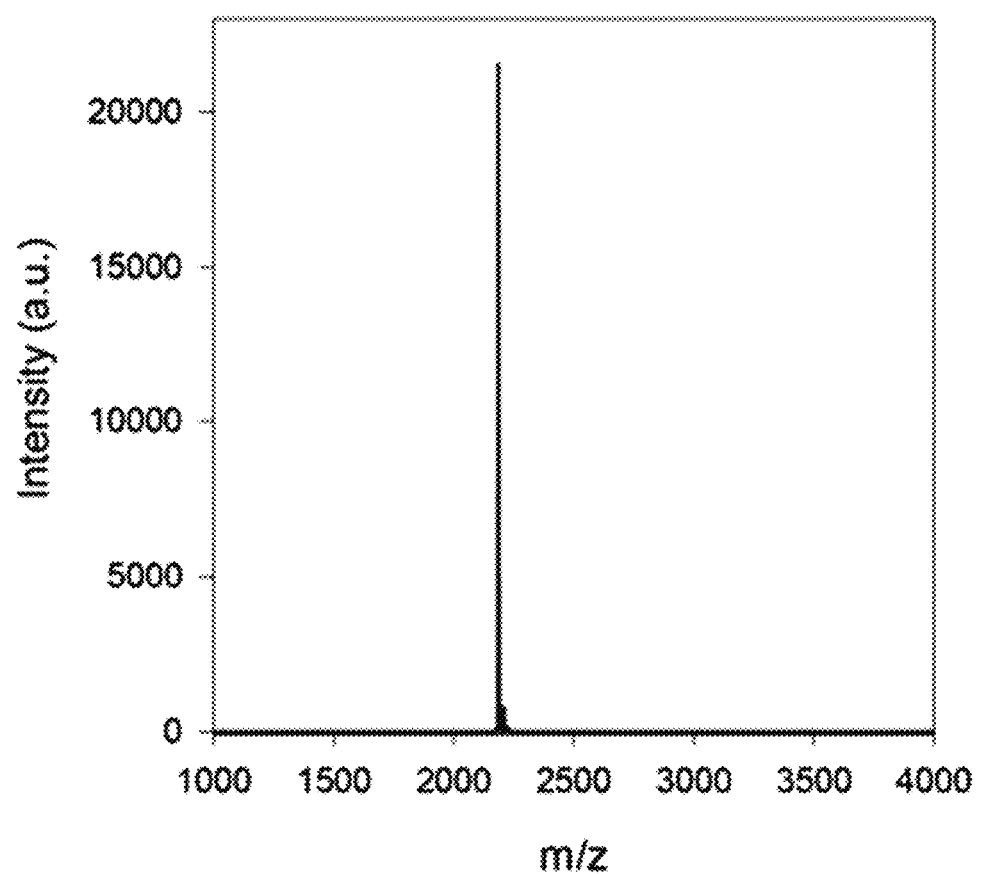
FIG. 17A shows the MALDI-TOF mass spectrum of an α-helix peptide substituted with an acryloyl group of Preparation Example 1.
Figure 17B:
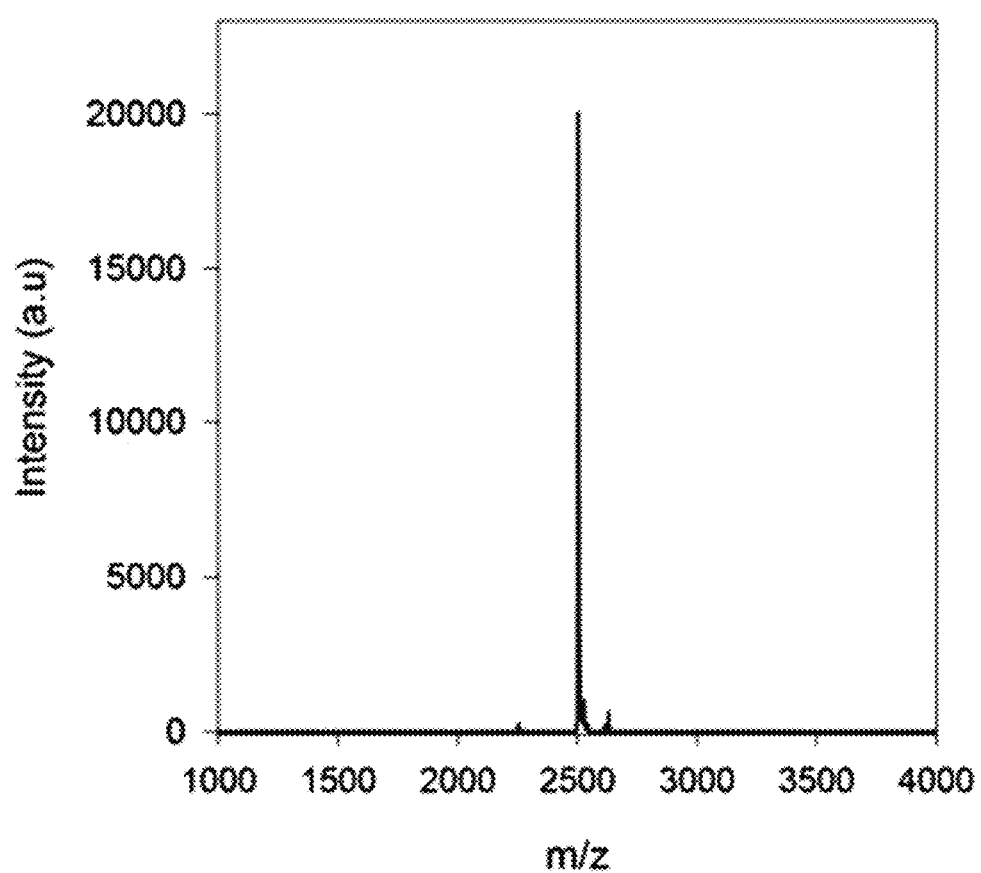
FIG. 17B shows the MALDI-TOF mass spectrum of an α-helix peptide substituted with an acryloyl group of Preparation Example 2.
Figure 17C:
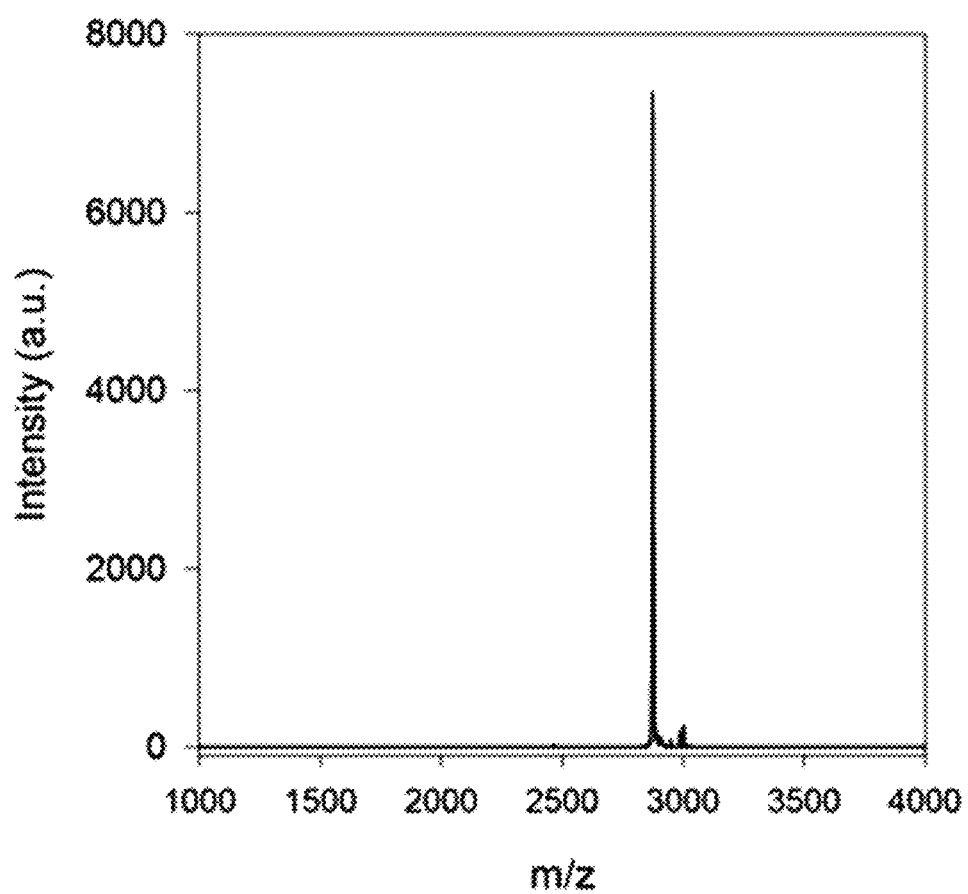
FIG. 17C shows the MALDI-TOF mass spectrum of an α-helix peptide substituted with an acryloyl group of Preparation Example 3.

In order to separate the synthesized peptide from the resin, the peptide fixed to the resin was treated with a cleavage cocktail (TFA: 1,2-ethanedithiol:thioanisole=95:2.5:2.5) for 4 hours. Then, after trituration using a tert-butyl methyl ether (TBME) solution, the obtained peptide was purified by reverse-phase HPLC (water-acetonitrile with 0.1% TFA). The molecular weight of the obtained peptide was investigated by matrix-assisted laser desorption/ionization (MALDI) time-of-flight mass spectrometry (Microflex LRF20, Bruker) (see FIGS. 17A, 17B and 17C).

Example 1: Preparation of Peptide-Polymer Conjugate

The peptide obtained in Preparation Example 1 and an acrylamide solution (100 mM) were mixed at a molar ratio of 1:100. After adding hexafluoro-2-propanol (HFIP) and water to a final concentration of 10% HFIP (vol %), reaction was performed for 1 hour. Polymerization was initiated by 1 μL of 10% ammonium persulfate (APS) and 1 μL of 10% tetramethylethylenediamine (TEMED) and conducted for 2 hours. The total reaction volume was 1 mL. A peptide-polymer conjugate was prepared by evaporating the HFIP and compensating for the volume loss with water.

Example 2: Preparation of Peptide-Polymer Conjugate in Distilled Water

A peptide-polymer conjugate was prepared in the same manner as in Example 1 except that the peptide obtained in Preparation Example 1 and an acrylamide solution (100 mM) were mixed at a molar ratio of 1:20 and only distilled water was added instead of the HFIP.

Example 3: Preparation of Peptide-Polymer Conjugate in Phosphate Buffer

A peptide-polymer conjugate was prepared in the same manner as in Example 1 except that a phosphate buffer (10 mM, pH 7.4) was added instead of the HFIP.

Example 4: Preparation of Peptide-Polymer Conjugate in Tris Buffer

A peptide-polymer conjugate was prepared in the same manner as in Example 1 except that a Tris buffer (15 mM, pH 7.5) was added instead of the HFIP.

Example 5: Preparation of Peptide-Polymer Conjugate

A peptide-polymer conjugate was prepared in the same manner as in Example 1 except that the peptide obtained in Preparation Example 2 was used instead of the peptide obtained in Preparation Example 1 and the peptide obtained in Preparation Example 2 and an acrylamide solution (100 mM) were mixed at a molar ratio of 1:20.

Comparative Example 1: Preparation of Peptide-Polymer Conjugate

A peptide-polymer conjugate was prepared in the same manner as in Example 1 except that the peptide obtained in Preparation Example 3 was used instead of the peptide obtained in Preparation Example 1 and the peptide obtained in Preparation Example 3 and an acrylamide solution (100 mM) were mixed at a molar ratio of 1:20.

Test Example 1: Circular Dichroism Spectroscopic Analysis 1

Because a peptide having an α-helix secondary structure has 3.6 residues per turn of the α-helix secondary structure and because i-th and (i+4)-th or i-th and (i+7)-th residues among them are arranged in the same direction, the peptide having the α-helix secondary structure wherein lysine residues are located at the above-described positions or the existing peptide having an α-helix secondary structure wherein the residues located at the above-described positions are substituted with lysine residues were used.

In this test example, peptide-polymer conjugates synthesized from the peptides having the α-helix secondary structure wherein lysine residues are located at the above-described positions (SEQ ID NOS 1 and 2) were used.

Specifically, SEQ ID NO 1 is a sequence derived from p53 peptide as an α-helix peptide having two lysine residues, with one lysine residue located at i-th position and the other lysine residue located at (i+7)-th position in the α-helix peptide.

The structure and stability of the α-helix peptide substituted with an acryloyl groups prepared in Preparation Examples 1-3 were analyzed.

Figure 3:
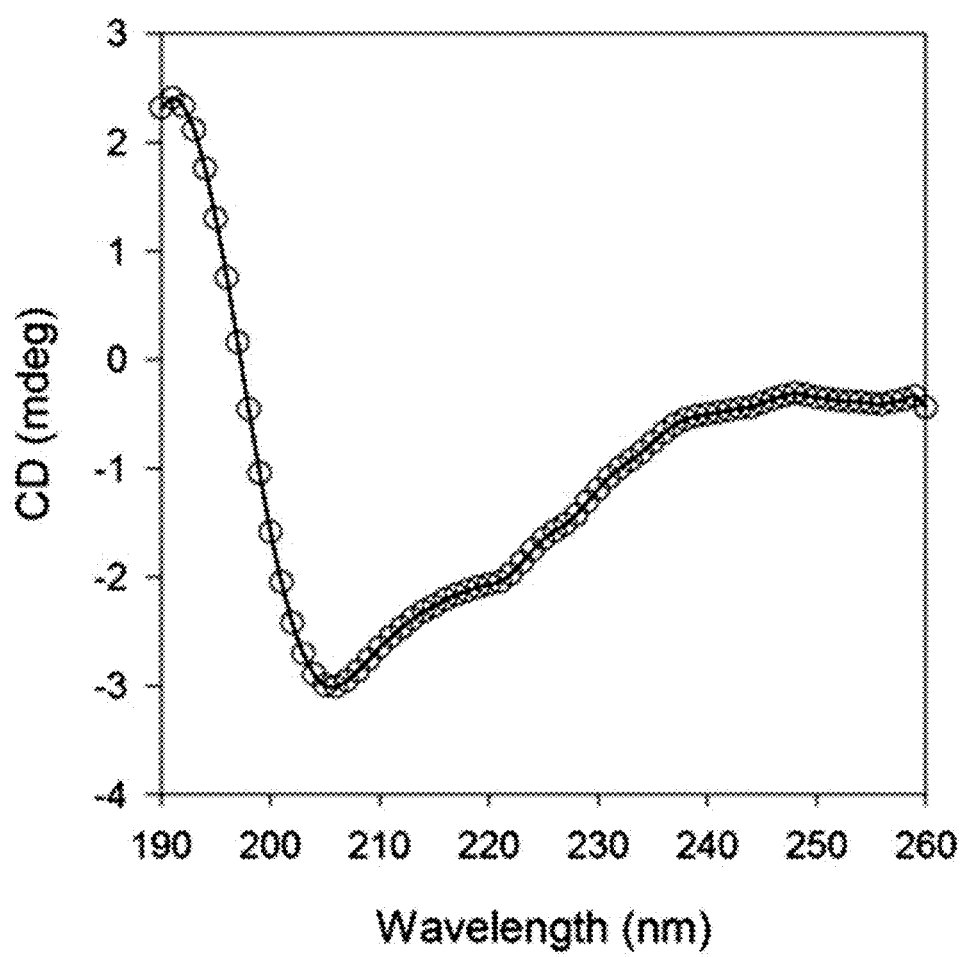
FIG. 3 shows the CD spectrum of an α-helix peptide substituted with an acryloyl group prepared in Preparation Example 1 in distilled water.
Figure 4:
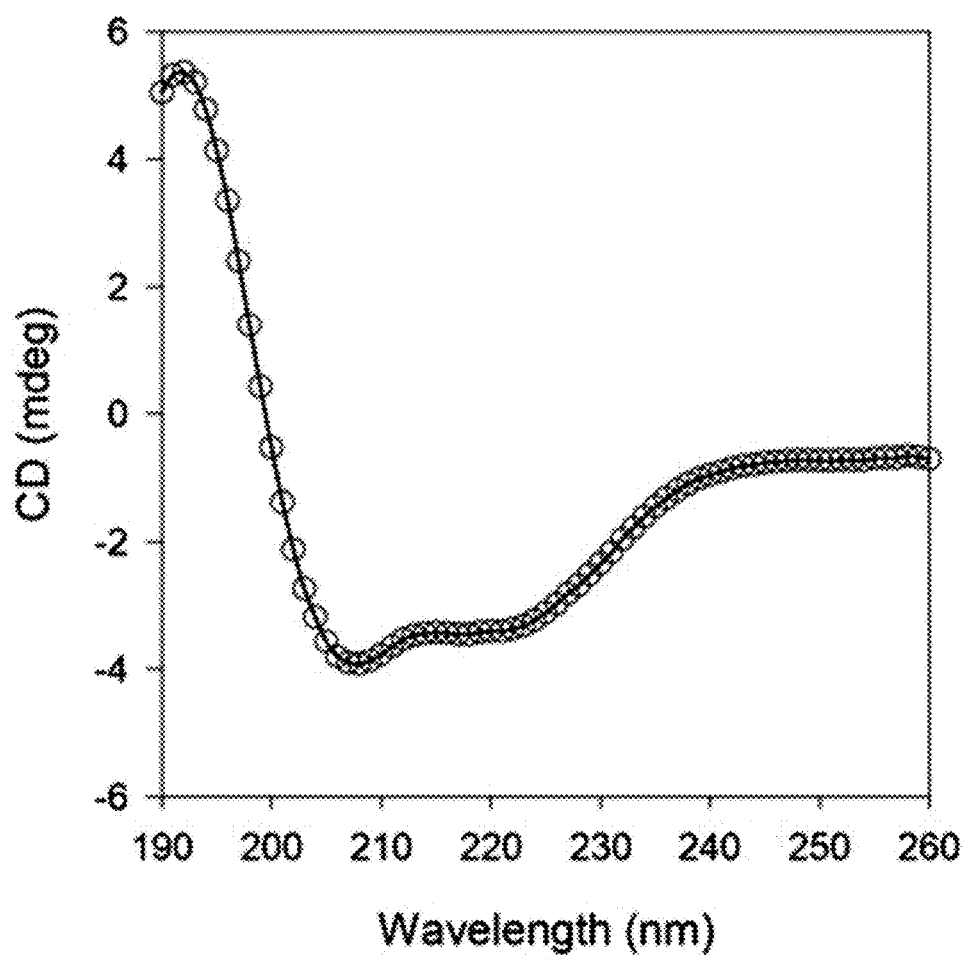
FIG. 4 shows the CD spectrum of an α-helix peptide substituted with an acryloyl group prepared in Preparation Example 1 in a 10% HFIP solution (HFIP:water=1:9, v/v).

FIG. 3 shows the CD spectrum of the α-helix peptide substituted with an acryloyl group prepared in Preparation Example 1 in distilled water and FIG. 4 shows the CD spectrum of the α-helix peptide substituted with an acryloyl group prepared in Preparation Example 1 in a 10% HFIP solution (HFIP:water=1:9, v/v).

The temperature was 25° C. and the peptide concentration was 6 μM.

As seen from FIG. 3, the α-helix secondary structure of the α-helix peptide substituted with an acryloyl group prepared in Preparation Example 1 (bisAAm-p53) was not stabilized but unfolded in distilled water.

In contrast, the α-helix secondary structure of the α-helix peptide substituted with an acryloyl group prepared in Preparation Example 1 was stabilized in the 10% HFIP solution as seen from FIG. 4. That is to say, it was confirmed that the α-helix secondary structure of the α-helix peptide substituted with an acryloyl group prepared according to the present disclosure is stabilized in the presence of a powerful α-helix inducing agent. This is confirmed by the negative bands observed at 208 nm and 222 nm in the CD spectrum, which indicate the α-helix secondary structure.

Test Example 2: Circular Dichroism Spectroscopic Analysis 2

The α-helix peptide substituted with an acryloyl group prepared in Preparation Example 1 (bisAAm-p53) was dissolved in a 10% HFIP solution (based on final concentration). After mixing with 100 molal acrylamide, a peptide-polymer conjugate was prepared through free radical induced polymerization by adding ammonium persulfate (APS) and N,N,N',N'-tetramethylethylenediamine (TEMED). The prepared 9 μM α-helix peptide multimer was diluted with a 0.2% HIFP solution.

Figure 5:
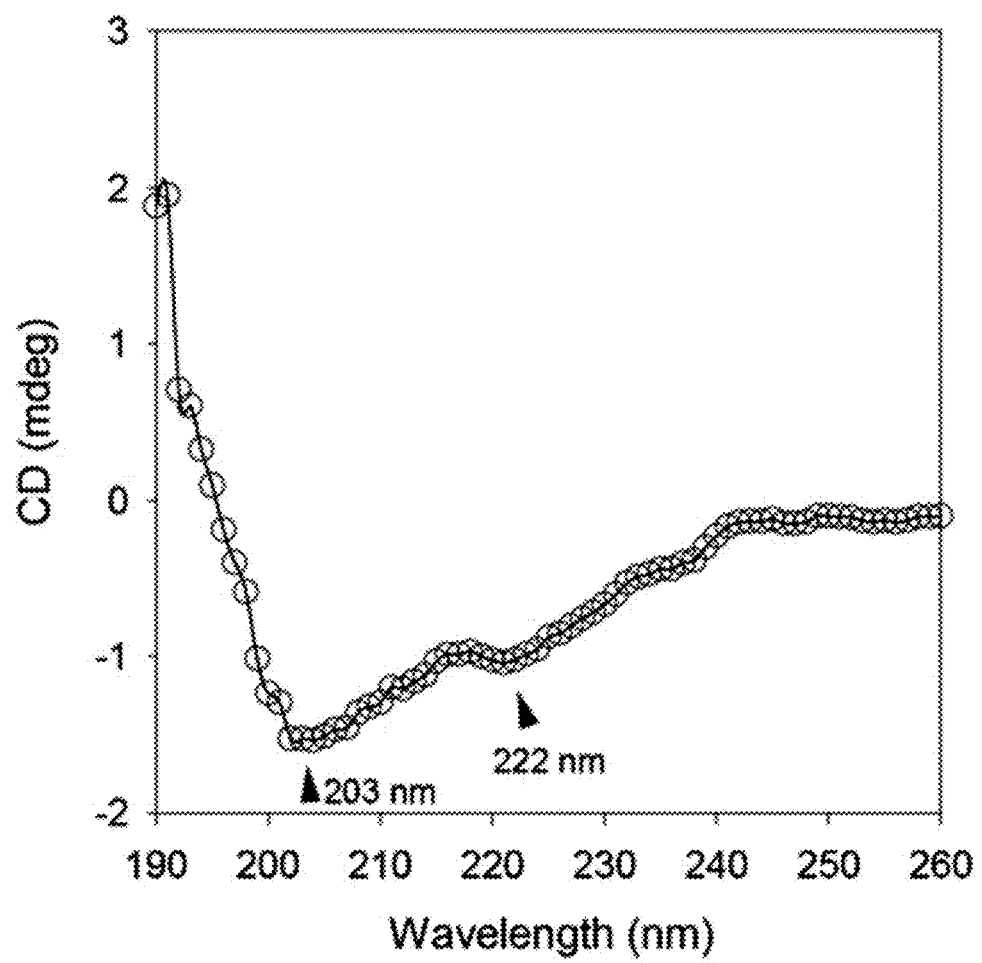
FIG. 5 shows the CD spectrum of a peptide-polymer conjugate prepared in Example 1 (9 μM).

FIG. 5 shows the CD spectrum of the peptide-polymer conjugate prepared in Example 1 (9 μM).

The circular dichroism (CD) spectroscopic analysis was conducted by the method described above.

As seen from FIG. 5, it was confirmed that the stability of the secondary structure of the peptide-polymer conjugate prepared in Example 1 was increased from the negative peaks distinctly observed at 203 nm and 222 nm and the blueshift of the positive maximum peak at 190 nm.

Because the 0.2% HFIP solution has no effect of substantially stabilizing the secondary structure of the α-helix peptide substituted with an acryloyl group prepared in Preparation Example 1 (bisAAm-p53) and the achiral polyacrylamide does not have any CD spectrum peak, it is certain that the 0.2% HFIP and the polyacrylamide do not have any effect on the CD spectrum FIG. 5.

That is to say, the stabilization of the secondary structure in the peptide-polymer conjugate prepared in Example 1 originates from the structure of the peptide-polymer conjugate, which may be because, while the α-helix peptide substituted with an acryloyl group prepared in Preparation Example 1 (bisAAm-p53) is polymerized through vinyl polymerization, a distance matching is formed due to the macrocyclization between the two acryloyl groups present in the α-helix peptide substituted with an acryloyl group prepared in Preparation Example 1 (bisAAm-p53) and therefore the stabilized secondary structure is fixed instantly (stapling polymerization).

Test Example 3: Circular Dichroism Spectroscopic Analysis 3

In order to quantitatively confirm the stabilization of the α-helix secondary structure in the peptide-polymer conjugate, each of the α-helix peptide substituted with an acryloyl group of Preparation Example 1 and the peptide-polymer conjugate of Example 1 was dissolved in 10% 2,2,2-trifluoroethanol (TFE) and the degree of α-helix secondary structure stabilization was measured at various temperatures using an α-helix secondary structure stabilizer less powerful than HFIP.

Figure 6:
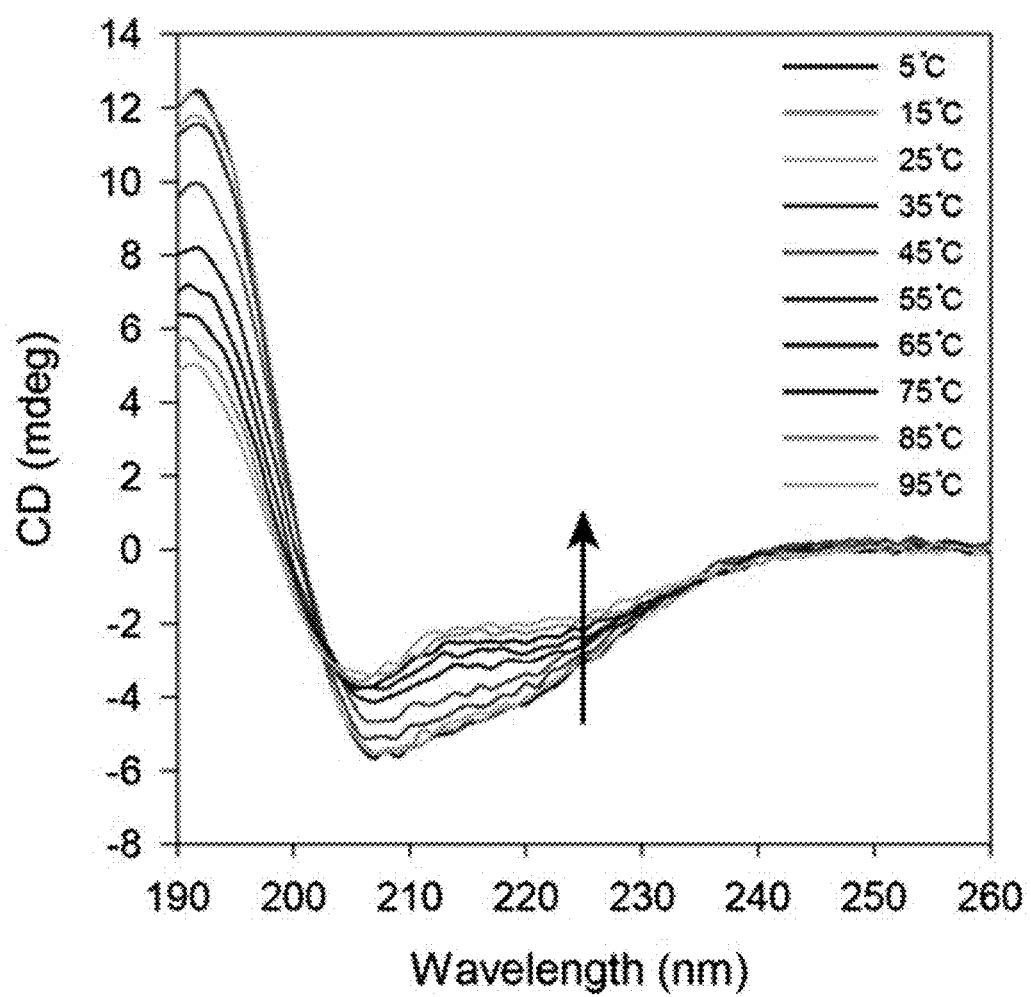
FIG. 6 shows the CD spectra of an α-helix peptide substituted with an acryloyl group of Preparation Example 1 at various temperatures.
Figure 7:
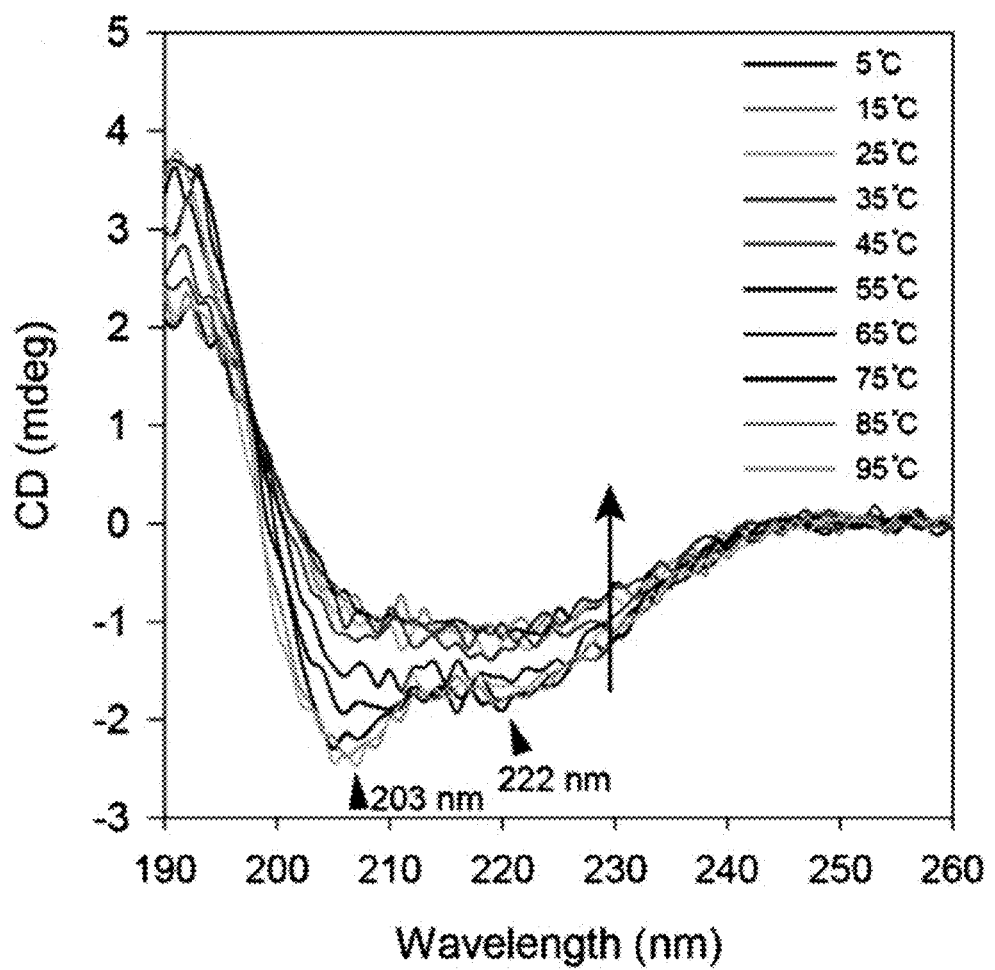
FIG. 7 shows the CD spectra of a peptide-polymer conjugate prepared in Example 1 at various temperatures.
Figure 8:
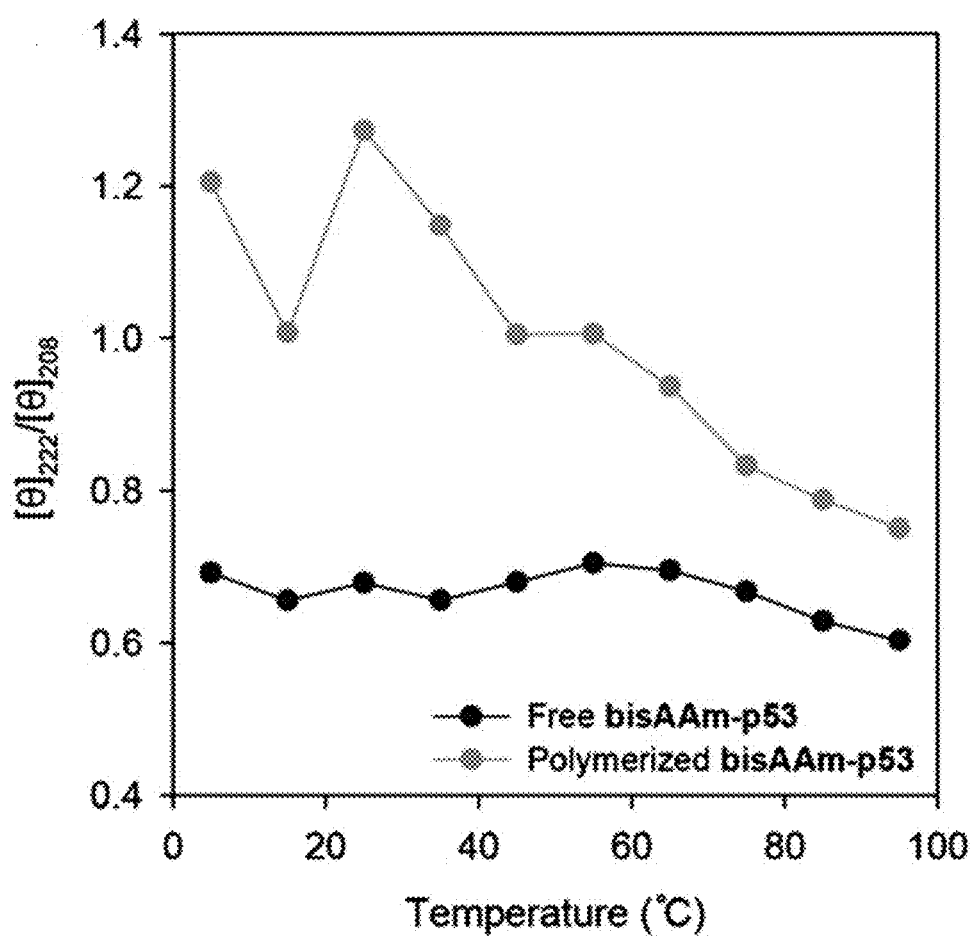
FIG. 8 shows $[\theta]_{222}/[\theta]_{208}$ ratios at different temperatures obtained from the CD spectra.

FIG. 6 shows the CD spectra of the α-helix peptide substituted with an acryloyl group of Preparation Example 1 (free bisAAm-p53) at various temperatures, FIG. 7 shows the CD spectra of the peptide-polymer conjugate prepared in Example 1 (polymerized bisAAm-p53) at various temperatures and FIG. 8 shows $[\theta]_{222}/[\theta]_{208}$ ratios at different temperatures obtained from the CD spectra. The molar ratio of bisAAm-p53:acrylamide was 1:100.

The circular dichroism (CD) spectroscopic analysis was conducted by the method described above.

As seen from FIGS. 6-8, the peptide-polymer conjugate prepared in Example 1 (FIG. 7) had higher $[\theta]_{222}/[\theta]_{208}$ ratios than the α-helix peptide substituted with an acryloyl group of Preparation Example 1 (FIG. 6) at all temperatures.

The $[\theta]_{222}/[\theta]_{208}$ ratio indicates the degree of the α-helix secondary structure in the peptide and the increase in the $[\theta]_{222}/[\theta]_{208}$ ratio means that the degree of the α-helix secondary structure increases.

In addition, the two negative peaks at 208 nm and 222 nm associated with the α-helix secondary structure were found only in the peptide-polymer conjugate (see FIG. 7). Accordingly, it was confirmed that the α-helix secondary structure in the peptide was stabilized more as the α-helix peptide substituted with an acryloyl group was polymerized into the peptide-polymer conjugate according to the present disclosure.

Test Example 4: Effect of Mole Fraction of α-Helix Peptide Substituted with Acryloyl Group of Preparation Example 1 on Stabilization of α-Helix Secondary Structure Before CD spectrum measurement, HFIP was completely evaporated from the samples through centrifugation.

Figure 9:
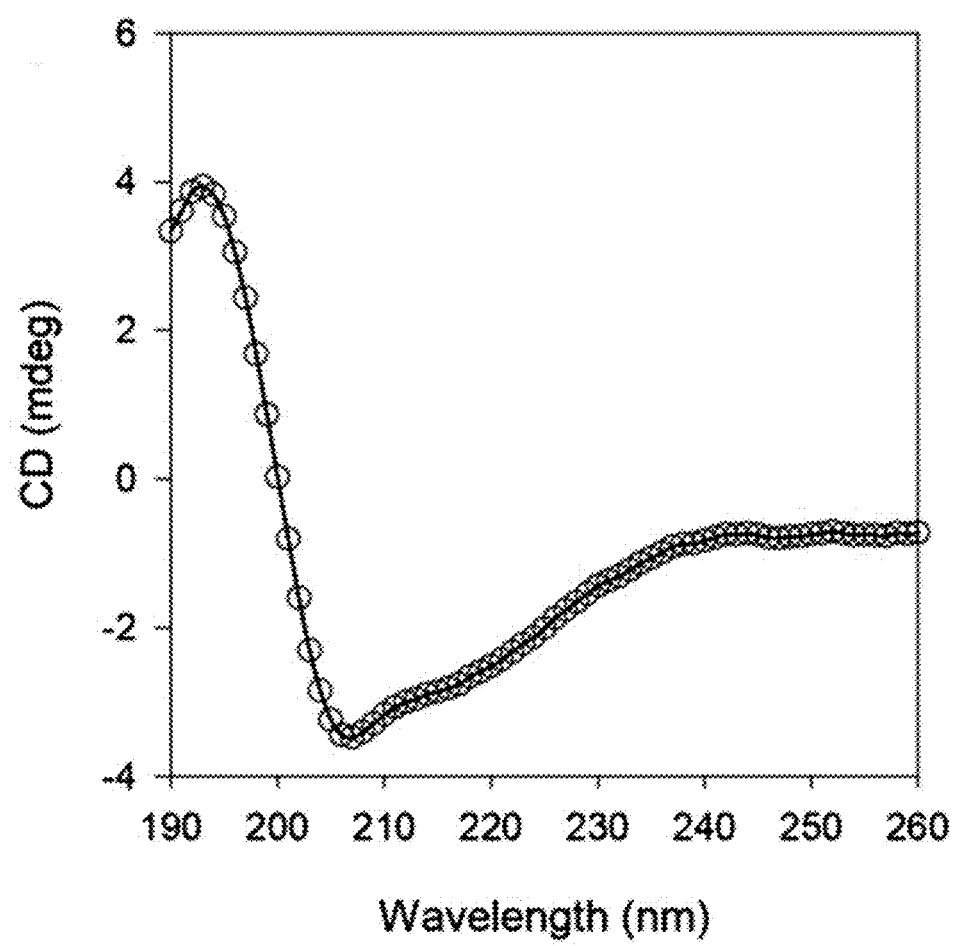
FIG. 9 shows the CD spectrum of an α-helix peptide substituted with an acryloyl group prepared in Preparation Example 1.
Figure 10:
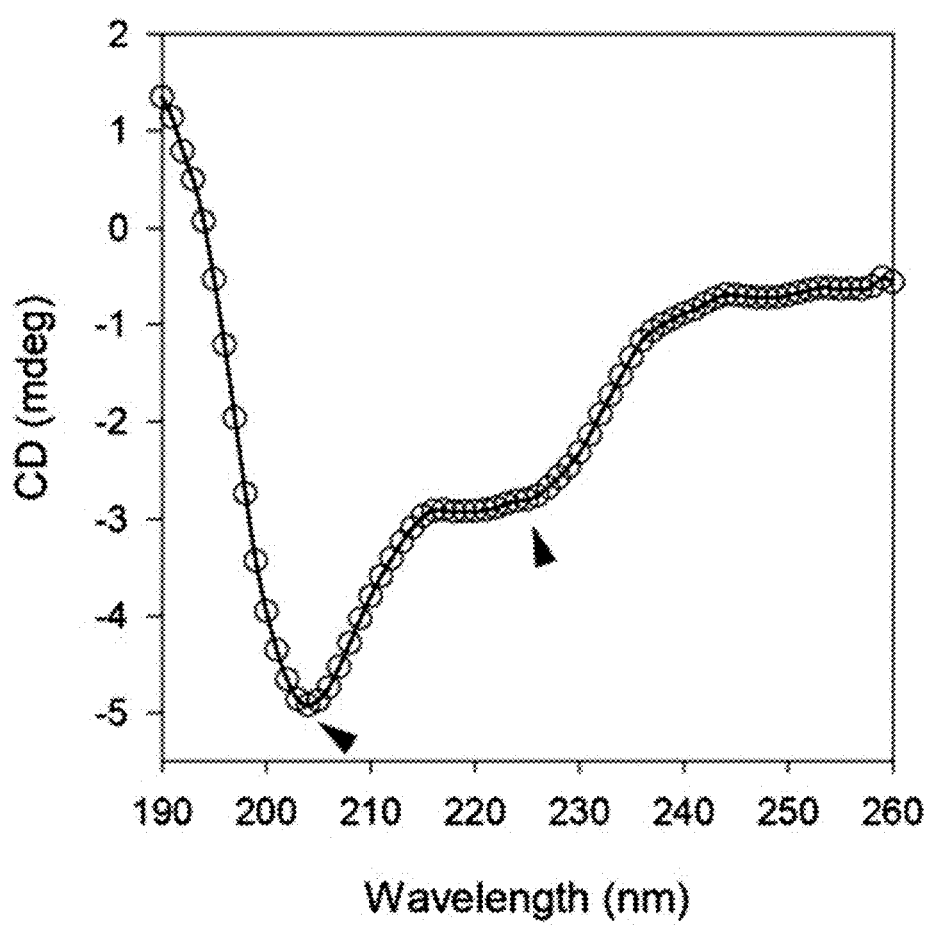
FIG. 10 shows the CD spectrum of a peptide-polymer conjugate of Example 2 prepared by polymerization in distilled water.
Figure 11:
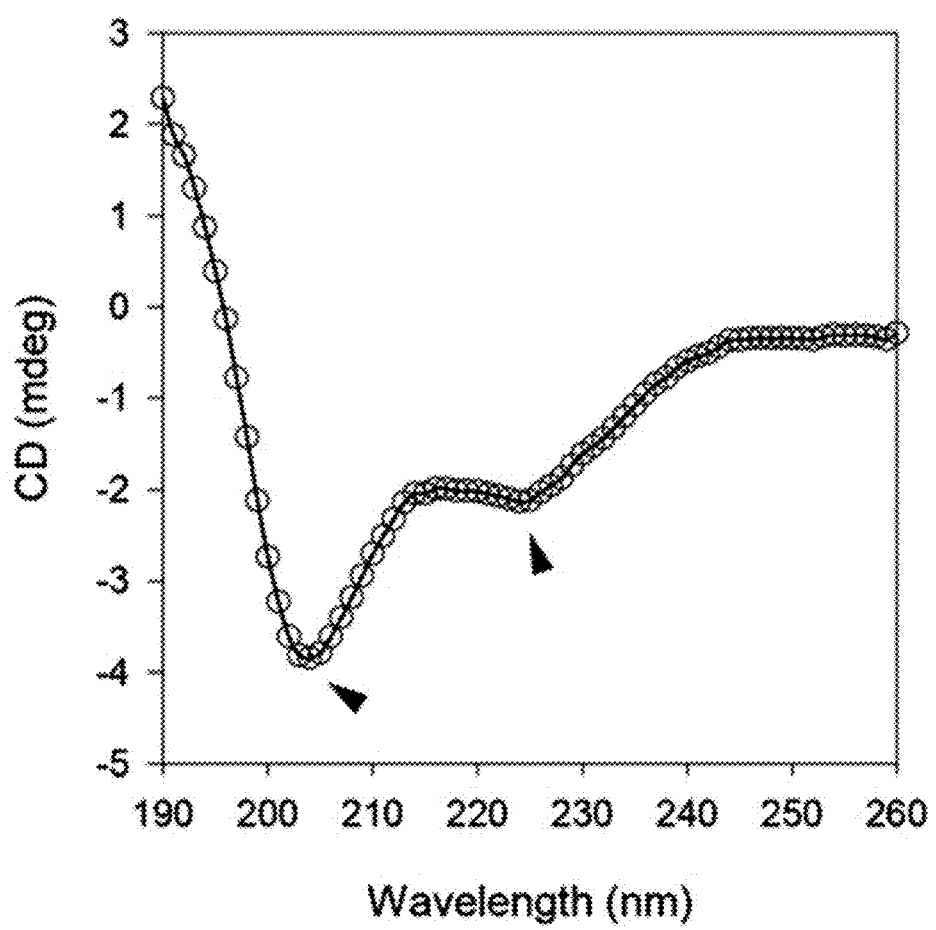
FIG. 11 shows the CD spectrum of a peptide-polymer conjugate of Example 3 prepared by conducting polymerization in a phosphate buffer.
Figure 12:
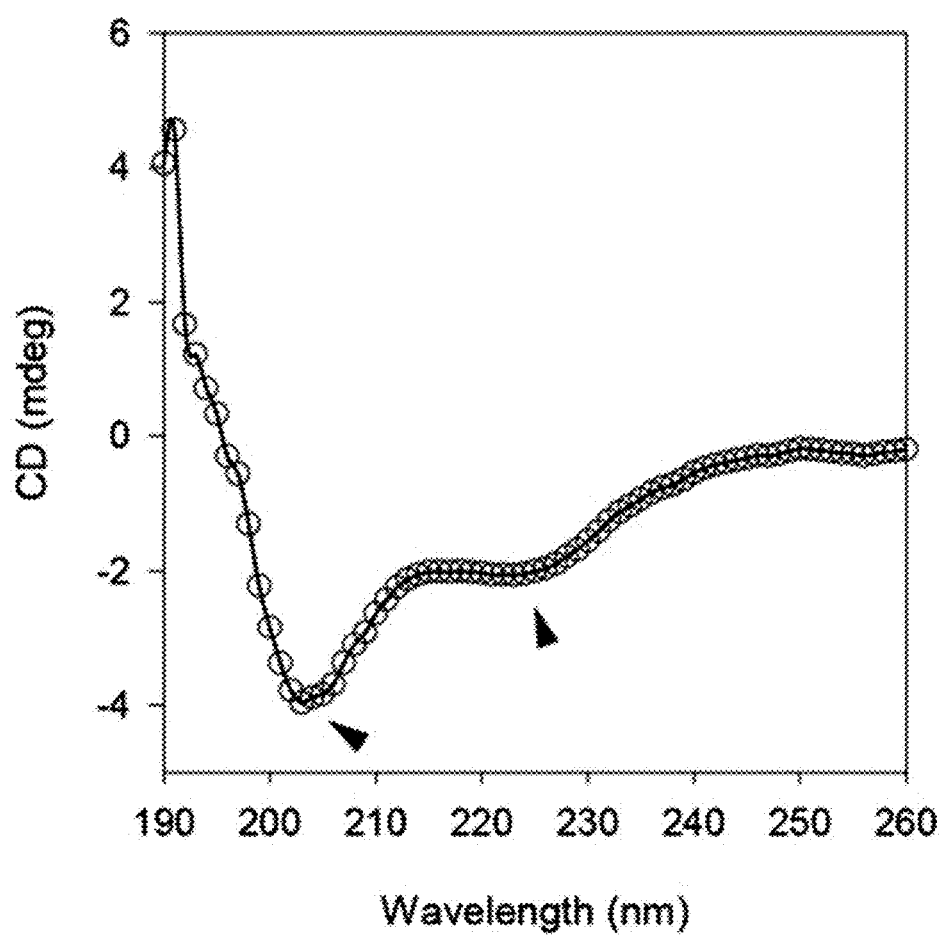
FIG. 12 shows the CD spectrum of a peptide-polymer conjugate of Example 4 prepared by conducting polymerization in a Tris buffer (15 mM, pH 7.5).

FIG. 9 shows the CD spectrum of the α-helix peptide substituted with an acryloyl group prepared in Preparation Example 1, FIG. 10 shows the CD spectrum of the peptide-polymer conjugate of Example 2 prepared by polymerization in distilled water, FIG. 11 shows the CD spectrum of the peptide-polymer conjugate of Example 3 prepared by conducting polymerization in a phosphate buffer and FIG. 12 shows the CD spectrum of the peptide-polymer conjugate of Example 4 prepared by conducting polymerization in a Tris buffer (15 mM, pH 7.5). The molar ratio of bisAAm-p53:acrylamide was 1:20.

As seen from FIG. 9-12, the α-helix secondary structure was stabilized when the mole fraction of the α-helix peptide substituted with an acryloyl group prepared in Preparation Example 1 was increased by 5%, as indicated by the two distinct negative peaks at 208 nm and 222 nm. This stabilization of the α-helix secondary structure is due to the stapling of the α-helix secondary structure of the peptide by the polymerization of the acryloyl group of the α-helix peptide substituted with an acryloyl group and the acrylamide.

In addition, it was confirmed that a multimer consisting of the peptides having stabilized α-helix secondary structure was prepared even under a physiological buffer condition. Accordingly, it can be seen that the peptide multimer having stabilized α-helix secondary structure can form peptide and polymer interactions under biological conditions.

Test Example 5: Circular Dichroism Spectroscopic Analysis 4

Because a peptide having an α-helix secondary structure has 3.6 residues per turn of the α-helix secondary structure and because i-th and (i+4)-th or i-th and (i+7)-th residues among them are arranged in the same direction, the peptide having the α-helix secondary structure wherein lysine residues are located at the above-described positions or the existing peptide having an α-helix secondary structure wherein the residues located at the above-described positions are substituted with lysine residues were used.

In this test example, the peptide-polymer conjugate synthesized using the peptide having α-helix secondary structure with lysine residues located at i-th and (i+4)-th positions (Preparation Example 3; SEQ ID NO 2) was used.

First, the stabilization of the α-helix secondary structure in α-helix peptide substituted with an acryloyl group prepared in Preparation Example 3 was investigated and it was compared with that of the α-helix secondary structure in the peptide-polymer conjugate prepared in Comparative Example 1 after polymerization.

Figure 13:
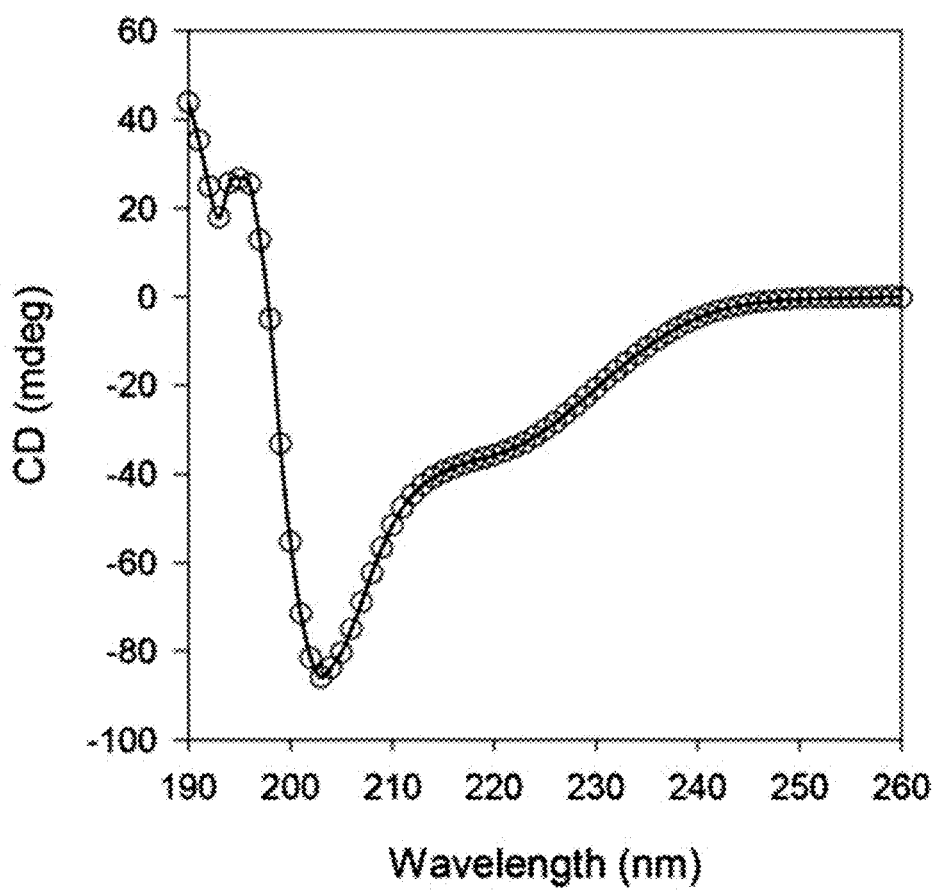
FIG. 13 shows the CD spectrum of an α-helix peptide substituted with an acryloyl group prepared in Preparation Example 3.
Figure 14:
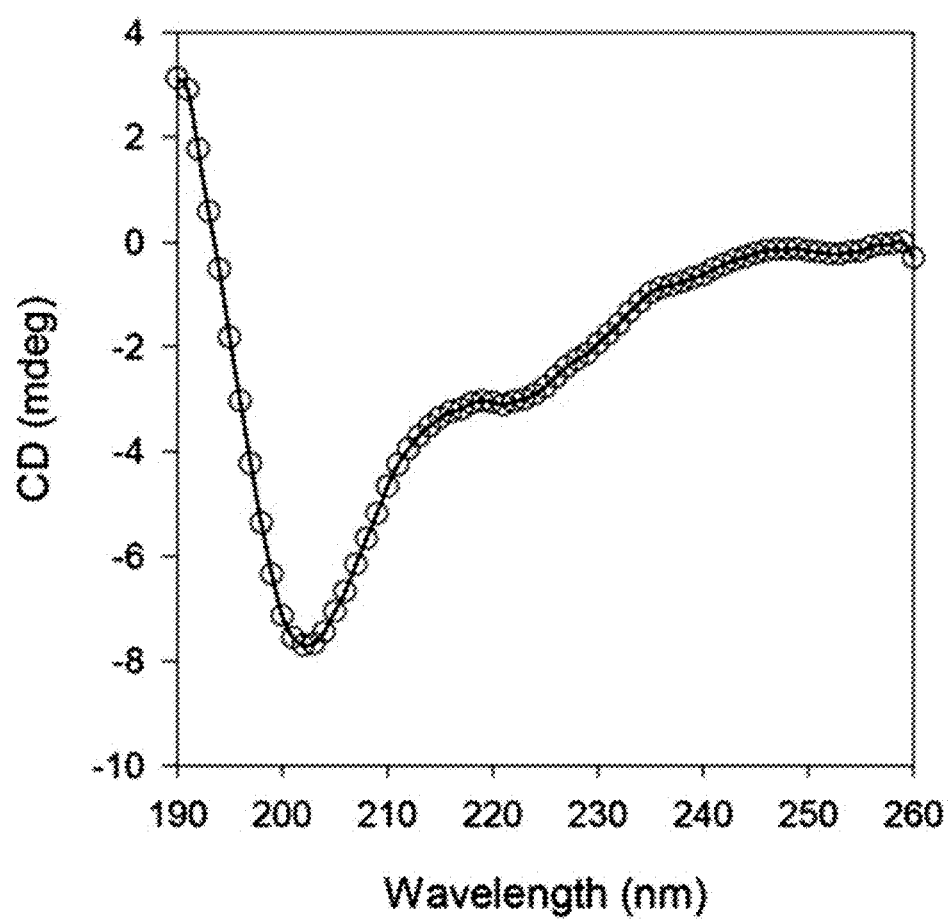
FIG. 14 shows the CD spectrum of a peptide-polymer conjugate prepared in Comparative Example 1.

FIG. 13 shows the CD spectrum of the α-helix peptide substituted with an acryloyl group prepared in Preparation Example 3 and FIG. 14 shows the CD spectrum of the peptide-polymer conjugate prepared in Comparative Example 1.

As seen from FIG. 13 and FIG. 14, the α-helix secondary structure of the α-helix peptide of Preparation Example 3, with lysine residues located at i-th and (i+4)-th positions and with the hydrogen of the side-chain amine group (ε-amine group) substituted with an acryloyl group, was not stabilized but unfolded.

Also, the α-helix secondary structure of the peptide-polymer conjugate of Comparative Example 1 polymerized from the α-helix peptide substituted with an acryloyl group of Preparation Example 3 was not stabilized.

That is to say, it can be seen that the α-helix secondary structure is stabilized only when the α-helix peptide has lysine residues located at i-th and (i+7)-th positions, the hydrogen of the side-chain amine group (ε-amine group) of the lysine residues at those positions is substituted with an acryloyl group and it is polymerized by adding acrylamide.

Test Example 6: SDS-PAGE Analysis

It needs to be investigated how a plurality of the α-helix peptides substituted with an acryloyl group prepared in Preparation Example 2 are polymerized, i.e. whether the peptide-polymer conjugate prepared in Example 5 is actually bound to acrylamide. It is because polyacrylamide is not detected in the CD spectrum and the peptide and polyacrylamide have different molecular characteristics.

But, a method commonly used to measure the molecular weight of polymers, e.g., size exclusion chromatography (SEC), is not applicable to investigate binding between peptide and the polyacrylamide in the peptide-polymer conjugate according to the present disclosure because standard reagents are not established.

Accordingly, the degree of polymerization (DP) of the peptide-polymer conjugate prepared in Example 5 was investigated instead.

Figure 15:
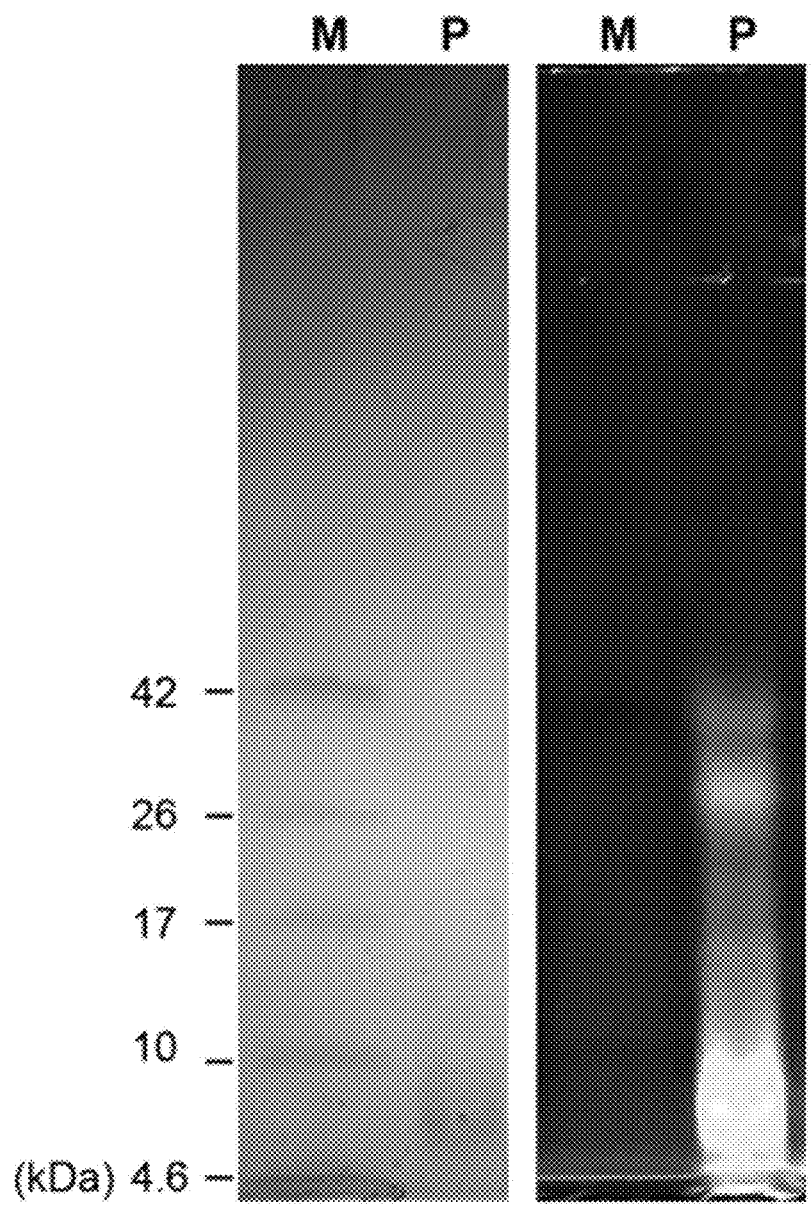
FIG. 15 shows an SDS-PAGE image of a protein marker and a peptide-polymer conjugate prepared in Example 5.

FIG. 15 shows the SDS-PAGE image of a protein marker and the peptide-polymer conjugate prepared in Example 5. In FIG. 15, M represents a protein marker and P represents the peptide-polymer conjugate prepared in Example 5. The image on the right side is a fluorescence image.

Because the α-helix peptide has a very small size, the peptide loaded on a gel cannot be visualized with commonly used stains. Therefore, a fluorescence-labeled α-helix peptide substituted with an acryloyl group as the one prepared in Preparation Example 2 was used.

When the peptide-polymer conjugate prepared in Example 5 was loaded on SDS-PAGE, a strong band was observed at 7 kDa and weak bands were observed at 30 kDa and 40 kDa, as seen from FIG. 15. This means that the molecular weight of the α-helix peptide substituted with an acryloyl group of Preparation Example 2 is 2.5 kDa.

From the SDS-PAGE analysis result shown in FIG. 15, it can be seen that the α-helix peptide substituted with an acryloyl group of Preparation Example 2 contains 3, 12 or 16 molecules.

To summarize, it can be seen that, through the single-step process according to the present disclosure, a peptide-polymer conjugate with a stabilized α-helix secondary structure wherein 3-16 peptides are fixed to one linear polymer can be obtained through stapling polymerization and the secondary structure of the peptide is stably constrained in the peptide-polymer conjugate.

While the present disclosure has been described with respect to the specific embodiments, it will be apparent to those skilled in the art that various changes and modifications may be made without departing from the spirit and scope of the disclosure as defined in the following claims.

What is claimed is:

1. A method for preparing a peptide-polymer conjugate, comprising:
   I) synthesizing an α-helix peptide substituted with an acryloyl group; and
   II) polymerizing the acryloyl group of the α-helix peptide substituted with an acryloyl group synthesized in I) into polyacrylamide by dissolving the α-helix peptide substituted with an acryloyl group synthesized in I), a water-soluble monomer and a polymerization initiator in a solvent,
   wherein the α-helix peptide substituted with an acryloyl group in I) is an α-helix peptide having at least two lysine residues, and
   two lysine residues in the α-helix peptide have the hydrogen of the side-chain amine group (ε-amine group) substituted with an acryloyl group.

2. The method for preparing a peptide-polymer conjugate according to claim 1, wherein the two lysine residues are necessarily formed at accurate positions in the α-helix peptide, with one lysine residue located at i-th position and the other lysine residue located at (i+7)-th position.

3. The method for preparing a peptide-polymer conjugate according to claim 2, wherein
   the α-helix peptide substituted with an acryloyl group in I) has the at least two lysine residues,
   two lysine residues are necessarily located at i-th position and (i+7)-th position in the α-helix peptide, and
   the hydrogen of the side-chain amine group (ε-amine group) of the lysine residues located at i-th position and (i+7)-th position is substituted with an acryloyl group.

4. The method for preparing a peptide-polymer conjugate according to claim 1, wherein the α-helix peptide having the at least two lysine residues is an α-helix peptide selected from a group consisting of SEQ ID NOS 1 to 10.

5. The method for preparing a peptide-polymer conjugate according to claim 1, wherein the solvent is one or more selected from a group consisting of a Tris buffer, a phosphate buffer, phosphoric acid, acetic acid, formic acid, hydrochloric acid, sulfuric acid, nitric acid, citric acid, hexafluoroisopropanol (HFIP), hexafluoropropanol (HFP), hexafluoroacetone (HFA), trifluoroacetic acid (TFA), diisopropylethylamine and methylimidazolium chloride.

6. The method for preparing a peptide-polymer conjugate according to claim 1, wherein the water-soluble monomer is selected from a group consisting of acrylamide, methacrylamide, N-hydroxymethylacrylamide, N,N-dimethylacrylamide, N-acetamidoacrylamide, 2-aminoethyl methacrylate, N,N-dimethylaminoethyl methacrylate, 2 hydroxyethyl acrylate, 2-hydroxyethyl methacrylate, 2-hydroxypropyl methacrylate, and combinations thereof.

7. The method for preparing a peptide-polymer conjugate according to claim 1, wherein the polymerization initiator is one or more selected from a group consisting of azobisisobutyronitrile (AIBN), ammonium persulfate (APS) and N,N,N',N'-tetramethylethylenediamine (TEMED).

8. The method for preparing a peptide-polymer conjugate according to claim 1, wherein the α-helix peptide substituted with an acryloyl group synthesized in I) and the water-soluble monomer are mixed at a molar ratio of 1:10 to 1:100.

9. The method for preparing a peptide-polymer conjugate according to claim 1, wherein the monomer is a water-soluble monomer selected from the group consisting of acrylamide, methacrylamide, acrylate, methacrylate, and combinations thereof.

10. The method for preparing a peptide-polymer conjugate according to claim 1, wherein the monomer is acrylamide.

11. An α-helix peptide substituted with an acryloyl group, wherein
    the α-helix peptide has at least two lysine residues, with one lysine residue located at i-th position and another lysine residue located at (i+7)-th position in the α-helix peptide, and
    the hydrogen of the side-chain amine group of the two lysine residues located at i-th position and (i+7)-th position is substituted with an acryloyl group.

12. The α-helix peptide substituted with an acryloyl group according to claim 11, wherein the α-helix peptide is one or more selected from SEQ ID NOS 1 to 10.

13. A peptide-polymer conjugate having a polymerized linear polymer formed from polymerization of the acryloyl group of the α-helix peptide substituted with an acryloyl group according to claim 11 and a water-soluble monomer as a main chain, wherein at least one α-helix peptide is fixed to the polymerized linear polymer.

14. The peptide-polymer conjugate according to claim 13, wherein the α-helix secondary structure of the α-helix peptide is stabilized.

15. The peptide-polymer conjugate according to claim 13, wherein the peptide-polymer conjugate has a $[\theta]_{208}/[\theta]_{222}$ ratio of 1-1.5 in a CD spectrum at 0-60° C.

16. The peptide-polymer conjugate according to claim 13, wherein the peptide-polymer conjugate maintains a $[\theta]_{208}/[\theta]_{222}$ ratio of 0.8 or greater in a CD spectrum at 0-100° C.

17. The peptide-polymer conjugate according to claim 13, wherein 3-20 α-helix peptides are fixed.

* * * * *

SEQUENCE LISTING

```
<160> NUMBER OF SEQ ID NOS: 10

<210> SEQ ID NO 1
<211> LENGTH: 16
<212> TYPE: PRT
<213> ORGANISM: Artificial Sequence
<220> FEATURE:
<223> OTHER INFORMATION: p53 peptide

<400> SEQUENCE: 1

Gln Ser Gln Gln Thr Phe Lys Asn Leu Trp Arg Leu Leu Lys Gln Asn
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: p53 peptide

<400> SEQUENCE: 2

Gln Ser Gln Gln Thr Phe Lys Asn Leu Trp Lys Leu Leu Lys Gln Asn
1               5                   10                  15

<210> SEQ ID NO 3
<211> LENGTH: 16
```

```
<212> TYPE: PRT
<213> ORGANISM: Artificial Sequence
<220> FEATURE:
<223> OTHER INFORMATION: p53 peptide

<400> SEQUENCE: 3

Leu Ser Gln Gln Thr Phe Lys Asn Leu Trp Arg Leu Leu Lys Gln Asn
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: p53 peptide

<400> SEQUENCE: 4

Leu Ser Gln Glu Thr Phe Lys Asn Leu Trp Lys Leu Leu Lys Gln Asn
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: p53 peptide

<400> SEQUENCE: 5

Leu Ser Gln Glu Thr Phe Lys Asp Leu Trp Lys Leu Leu Lys Glu Asn
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: p53 peptide

<400> SEQUENCE: 6

Leu Ser Gln Lys Thr Phe Ser Asp Leu Trp Lys Leu Leu Pro Glu Asn
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: p53 peptide

<400> SEQUENCE: 7

Leu Ser Gln Glu Lys Phe Ser Asp Leu Trp Lys Lys Leu Pro Glu Asn
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: p53 peptide

<400> SEQUENCE: 8

Leu Ser Gln Glu Thr Phe Ser Asp Lys Trp Lys Leu Leu Pro Glu Lys
1               5                   10                  15

<210> SEQ ID NO 9
<211> LENGTH: 16
<212> TYPE: PRT
```

```
<213> ORGANISM: Artificial Sequence
<220> FEATURE:
<223> OTHER INFORMATION: p53 wild type peptide

<400> SEQUENCE: 9

Leu Ser Gln Glu Thr Phe Lys Asp Lys Trp Arg Leu Leu Lys Gln Asn
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: p53 wild type peptide

<400> SEQUENCE: 10

Gln Ser Gln Gln Thr Phe Lys Asn Leu Trp Arg Lys Lys Lys Gln Asn
1               5                   10                  15
```